United States Patent [19]

Cragoe, Jr. et al.

[11] Patent Number: 4,634,717
[45] Date of Patent: Jan. 6, 1987

[54] SUBSTITUTED-3-(2,3-DIHYDRO-1H-INDEN-5-YL)-4-HYDROXY-1H-PYRROLE-2,5-DIONES, USEFUL FOR TREATING PERSONS WITH GRAY MATTER EDEMA

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 605,738

[22] Filed: May 1, 1984

[51] Int. Cl.[4] ..................... A61K 31/40; C07D 207/40
[52] U.S. Cl. .................................... 514/425; 544/404; 548/545
[58] Field of Search ........................ 548/545; 544/404; 514/425

[56] References Cited

U.S. PATENT DOCUMENTS 4,070,539  1/1978  Cragoe et al. ..................... 548/544
4,256,758  3/1981  Cragoe et al. ..................... 548/544
4,342,776  8/1982  Cragoe et al. ..................... 548/544

OTHER PUBLICATIONS

Cragoe et al, Chem. Abst. 97:127490t.
Rooney et al, Chem. Abst. 99:147x.
Cragoe et al, J. Med. Chem. 1982, 25, 567–579.
Burger, Medicinal Chem. 2nd edition, 1960, pp. 42, 43.

*Primary Examiner*—Donald G. Daus
*Assistant Examiner*—Cecilia Shen
*Attorney, Agent, or Firm*—C. M. Caruso; T. E. Arther; H. J. Pfeiffer

[57] ABSTRACT

The invention relates to novel substituted-3-(2,3-dihydro-1H-inden-5-yl)-4-hydroxy-1H-pyrrole-2,5-diones, their analogs and their salts. These compounds are synthesized by methods selected from a number of synthetic routes depending on the particular structure, choice of intermediate or preferred reaction sequence. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections and various brain concussions.

1 Claim, No Drawings

SUBSTITUTED-3-(2,3-DIHYDRO-1H-INDEN-5-YL)-4-HYDROXY-1H-PYRROLE-2,5-DIONES, USEFUL FOR TREATING PERSONS WITH GRAY MATTER EDEMA

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cereral infections and various concussions results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

A recent publication entitled "Agents for the Treatment of Brain Injury" 1. Aryloxyalkanoic Acids, Cragoe et al, J. Med. Chem., (1982) 25, 567–79, reports on recent experimental testing of agents for treatment of brain injury and reviews the current status of treatment of brain injury.

In addition, some compounds having structures related to the compounds of the present invention have been reported as being useful in the treatment and prevention of calcium oxalate kidney stone formation in U.S. Pat. No. 4,342,776 of Cragoe et al. There is, however, no suggestion in the patent that any of the compounds disclosed therein would be of use in the treatment of brain injury.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural formula (I).

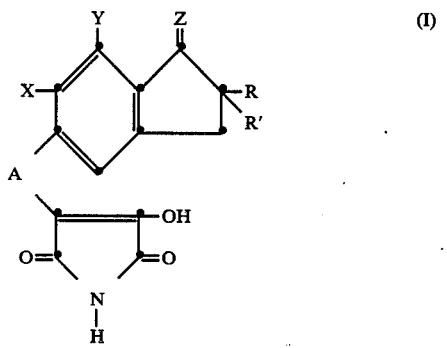

Wherein R is cycloalkyl ($C_3$ to $C_6$), cycloalkyllower alkyl ($C_4$ to $C_7$ total), aryl, such as phenyl, substituted aryl, such as phenyl with substituents, such as halo, methyl, methoxy, and hydroxy, heterocyclic, such as thienyl, aralkyl, such as benzyl and phenethyl, lower alkyl, branched or unbranched, lower alkenyl, branched or unbranched and lower alkynyl and the like. $R^1$ is lower alkyl, branched or unbranched, alkenyl or alkynyl and the like. X and Y are chloro or methyl and the like and A is a bond, —O—, or —O(CH$_2$)$_q$, where q is 1 to 5 and Z is O or H and OH.

When the R and $R^1$ substituents are different, the 2-position carbon atom of the indane ring is asymmetric and these compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

An example of this is seen with the compound of Example 1, which is (+)-3-(6,7-dichloro-2-cyclopentyl-2,3-dihydro-2-methyl-1-oxo-1H-inden-5-yl)-4-hydroxy-1H-pyrrole-2,5-dione 1-methylpiperazine salt which is much more active than the (−)-enantiomer described in Example 23. Thus, by using the pure (+)-enantiomer, not only has the much less active component of the racemate been eliminated but its unwanted contribution to toxicity and side effects abolished and its detrimental effect on intrinsic activity has been eliminated.

With the compounds where Z is H and OH, i.e. those where there is a hydroxy group on the 1-position of the indane ring, a second asymmetric carbon atom (the 1-position of the indane ring) is established. Therefore, the compounds where Z is H and OH and R and $R^1$ are different consist of two diastereomers, each of which is a racemate. However, the diastereomers can be separated by fractional crystallization or chromatography. When intermediates which are preresolved at the 2-position of the indane ring, reduction of a 1-indanone to a 1-indanol produces two diastereomers, each consisting of a single enantiomer, which can be separated by fractional crystallization or chromatography. This type of compound is illustrated by Examples 32 and 33.

Since the products of the invention are acidic, the invention also includes the obvious pharmaceutically acceptable salts, such as the sodium, potassium, ammonium, trimethylammonium, piperazinium, 1-methylpiperazinium, guanidinium, bis-(2-hydroxyethyl)ammonium, N-methylglucosamonium and the like salts.

It is also to be noted that the compounds of Formula I, as well as their salts of Formula I-G, often form solvates with the solvents in which they are prepared or from which they are recrystallized. These solvates may be used per se or they may be desolvated by heating (e.g. at 70° C.) in vacuo.

Although the invention primarily involves novel substituted-3-(2,3-dihydro-1H-inden-5-yl)-4-hydroxy-1H-pyrrole-2,5-diones, and their salts, it also includes their derivatives, such as oximes, hydrazones and the like.

In accordance with one aspect of the present invention, there is included a novel group of compounds which are pure enantiomers of compounds of Formula I-A:

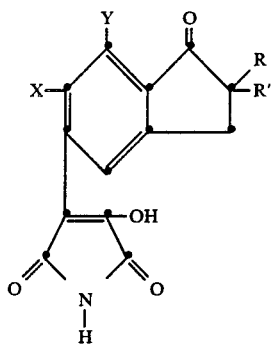

(I-A)

wherein X, Y, R and R' are defined as hereinabove, provided that R and R' are not the same entities, and the pharmaceutically acceptable salts thereof, as well as pharmaceutical compositions in unit dosage form containing an effective amount of one of the compounds encompassed by the above formula and the method of treating brain injury using one of said pharmaceutical compositions.

Also included in this aspect of the invention are novel racemic compounds in which R is cycloalkyl, cycloalkyl-lower alkyl, aryl selected from phenyl, halophenyl, methoxyphenyl, hydroxyphenyl, heterocyclic, including thienyl, aralkyl selected from benzyl and phenethyl, lower alkyl, lower alkenyl, lower alkynyl; and R' is lower alkyl, lower alkenyl or lower alkynyl, provided that R is not cycloalkyl or alkyl when R' is lower alkyl and both X and Y are chloro, and the method of treating grain injury using said novel racemic compounds.

In accordance with a second aspect of the present invention, there is included a novel group of diastereomers and their enantiomers of compounds of Formula I-B:

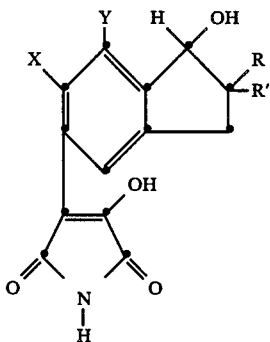

(I-B)

wherein X, Y, R and R' are as defined hereinabove, provided that R and R' are not the same entities, said diastereomers being derived by reduction of a pure enantiomer, particularly the pure (+)-enantiomer of the corresponding 1-oxo compound, as well as pharmaceutical compositions in unit dosage form containing an effective amount of one of the compounds encompassed by a diastereomer of the above formula. Also included are the corresponding racemic compounds wherein, X, Y, R and R' are defined as hereinabove provided that R is not cycloalkyl or alkyl when R' is lower alkyl and X and Y are both chloro.

In accordance with a third aspect of the present invention, there is included a novel group of compounds of Formula I-C:

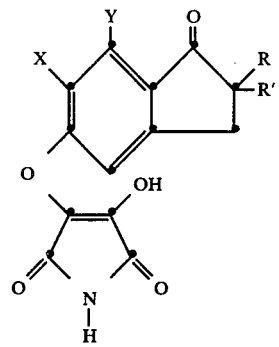

(I-C)

wherein X, Y, R and R' are as defined hereinabove including, when R and R' are different entities, the racemic compounds and the (+)-enantiomers of said racemic compounds and pharmaceutical compositions in unit dosage form containing an effective amount of one of the defined compounds or a (+)-enantiomer thereof.

In accordance with a fourth aspect of the present invention, there is included a novel group of diastereomers and their enantiomers of Formula I-D:

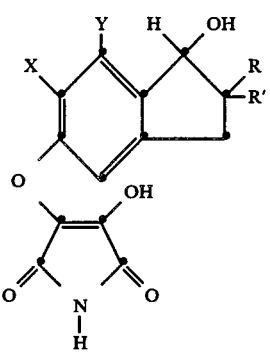

(I-D)

said diastereomers being derived by reduction of the pure enantiomer, especially the pure (+)-enantiomer of the corresponding 1-oxo compound, as well as pharmaceutical compositions in unit dosage form containing an effective amount of one of the novel derived diastereomers. Also included are the corresponding racemic compounds wherein X, Y, R and R' are defined as hereinabove provided that R is not cycloalkyl or alkyl when R' is lower alkyl or cycloalkyl and X and Y are both chloro.

In accordance with a fifth aspect of the present invention, there is provided a novel group of compounds of Formula I-E:

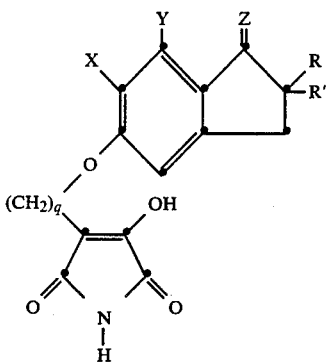

(I-E)

wherein Z, X, Y, R, R' and q are as defined hereinabove and the optical isomers thereof, wherein R and R' are different entities, and/or Z is H and OH, as well as pharmaceutical compositions in unit dosage form containing an effective amount of a compound of the above formula or a pure enantiomer, particularly the (+)-enantiomer or diastereoisomer derived therefrom by reduction of the corresponding 1-oxo compound.

PREFERRED EMBODIMENT OF THE INVENTION

The preferred embodiments of the instant invention are realized in structural Formula I-F wherein:

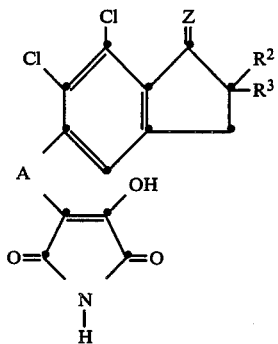

(I-F)

$R^2$ is cyclopentyl, phenyl or benzyl

Z is as defined before.

$R^3$ is lower alkyl, alkenyl and alkynyl, and $A^1$ is a bond, —O—, and $O(CH_2)_q$- where q is 1 to 4.

Also included are the diastereomers and the enantiomers of each racemate.

Preferred compounds are (+)-3-(6,7-dichloro-2-cyclopentyl-2,3-dihydro-2-methyl-1-oxo-1H-inden-5-yl)-4-hydroxy-1H-pyrrole-2,5-dione and its nontoxic salts.

Other preferred compounds are 3-(2-butyl-6,7-dichloro-2-cyclopentyl-2,3-dihydro-2-methyl-1-oxo-1H-inden-5-yl)-4-hydroxy-1H-pyrrole-2,5-dione, and its (+)-enantiomer and their pharmaceutically acceptable salts.

Other preferred compounds are 3-[2-((6,7-dichloro-2-cyclopentyl-2,3-dihydro-2-methyl-1-oxo-1H-inden-5-yl)oxy)ethyl]4-hydroxy-1H-pyrrole-2,5-dione.

Other preferred compounds are 3-(6,7-dichloro-2,3-dihydro-2-methyl-1-oxo-2-phenyl-1H-inden-5-yl)-4-hydroxy-1H-pyrrole-2,5-dione, its (−)enantiomer and their pharmaceutically acceptable salts.

Other preferred compounds include 3-(6,7-dichloro-2-cyclopentyl-2,3-dihydro-1-hydroxy-2-methyl-1H-inden-5-yl)-4-hydroxy-1H-pyrrole-2,5-dione, its (+)-α-diastereomer and the (+)-β-diastereomer (each of which are pure enantiomers) and their pharmaceutically acceptable salts.

Other preferred compounds include 3-[2-((6,7-dichloro-2-cyclopentyl-2,3-dihydro-1-hydroxy-2-methyl-1H-inden-5-yl)oxy)ethyl]-4-hydroxy-1H-pyrrole-2,5-dione, its (+)-α-diastereomer, its (+)-β-diasterisomer (each of which are pure enantiomers) and their pharmaceutically acceptable salts.

Other preferred compounds include the (+)-α-diastereomer and (+)-β-diastereomer of 3-[2-(6,7-dichloro-2-cyclopentyl-2,3-dihydro-1-hydroxy-2-methyl-1H-inden-5-yl)oxy]-4-hydroxy-1H-pyrrole-2,5-dione, each of which consists of a single pure enantiomer.

Especially preferred are the pure enantiomers since, in most instances, one enantiomer is more active biologically then its antipode.

Included within the scope of this invention are the pharmaceutically acceptable salts of the parent 3-substituted-4-hydroxy-1H-pyrrole-2,5-diones since a major medical use of these compounds is solutions of their soluble salts which can be administered parenterally.

Thus, the acid addition salts can be prepared by the reaction of the 3-substituted-4-hydroxy-1H-pyrrole-2,5-diones of this invention with an appropriate amine, ammonium hydroxide, guanidine, alkali metal hydroxide, alkali metal carbonate, alkali metal bicarbonate, quaternary ammonium hydroxide and the like. The salts selected are derived from among the non-toxic, pharmaceutically acceptable bases.

The synthesis of the 3-substituted-4-hydroxy-1H-pyrrole-2,5-diones of Formula I are generally carried out by the reaction of the appropriate amide (Formula II) with diethyl oxalate in the presence of a base and a solvent.

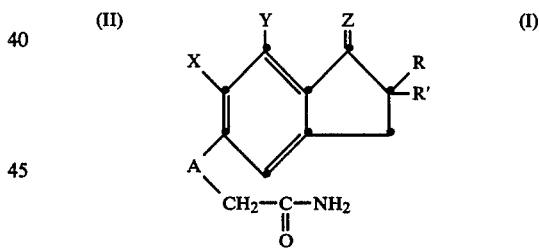

Advantageously, the base that is used can be potassium tert.-butoxide but other bases, such as sodium ethoxide or potassium methoxide can be used. The use of dimethylformamide is especially advantageous as a solvent but other polar, inert solvents such as 1-methyl-2-pyrrolidinone can be used. The reaction is generally conducted at the ambient temperature but it can be conducted at temperatures as low as 10° C. and as high as 50° C. for periods of time of 6 to 24 hours, depending on the specific reactants.

The reaction can be conducted using amides of Formula II which are mixtures of diastereomers, pure diastereomers, racemates or pure enantiomers and, thus, obtain the corresponding 3-substituted-4-hydroxy-1H-pyrroline-2,5-diones of Formula I as mixtures of diastereomers, pure diastereomers, racemates or pure enantiomers.

Some 3-(2,3-dihydro-1-oxo-1H-inden-5-yl)-4-hydroxy-1H-pyrrole-2,5-diones of the instant invention are advantageously prepared by the oxidation of the corresponding 3-(2,3-dihydro-1-hydroxy-1H-inden-5-yl)-4-hydroxy-1H-pyrrole-2,5-diones. Advantageously this is carried out using an oxidizing agent, such as Jones reagent ($CrO_3$ in dilute sulfuric acid) using a solvent, such as acetone, 2-butanone, and the like. The reaction is generally conducted at ambient temperatures but temperatures in the range of 10° to 40° C. can be used.

The preparation of the intermediate amides of formula II is carried out by any one of several methods involving the reaction of the appropriate ester Formula III, acid chloride of Formula IV or acylimidazole of Formula V with ammonia.

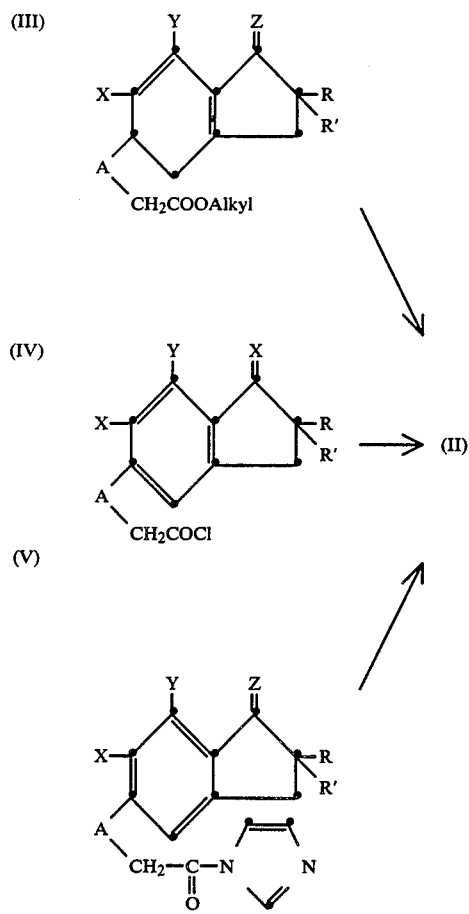

The reaction of an ester of Formula III is generally carried out in a solvent such as dimethylformamide or 1-methyl-2-pyrrolidinone and then ammonia in a solvent, such as methanol or ethanol, is added. Ambient temperature is advantageously employed but temperatures as low as 10° C. or as high as 100° C. can be used; however, when higher temperatures are employed, it is necessary to use a sealed vessel to contain the ammonia. The reaction time varies, depending on the temperature and may require from twelve hours to four weeks.

When an acid chloride of Formula IV is used, the reaction is generally conducted in an inert solvent, such as methylene chloride or benzene and the ammonia added in a solvent like ether or a mixture of ether and methylene chloride. Usually it is also advantageous to introduce ammonia gas and finally aqueous ammonia. The reaction is generally conducted at temperatures in the range of 0° C. to 10° C. but, if a sealed reaction vessel is used, remperatures of 10° to 50° C. can be used. The reaction times are generally in the range of 10 minutes to two hours.

When an amide of Formula II is prepared from an acylimidazole of Formula V, a solvent, such as tetrahydrofuran or dioxane is employed since the acylimidazole is generated in that solvent. Then, the acylimidazole is treated with ammonia gas or aqueous ammonia. The reaction is generally carried out at ambient temperature but temperatures as low as 10° C. or as high as 50° C. can be used.

The preparation of amides of Formula II-A, i.e. those in which Z=H+OH are best prepared by reduction of the corresponding compound of Formula II-B where Z=O. The reduction is advantageously conducted using sodium borohydride in a solvent like ethanol at room temperature for a period of 1 to 5 hours.

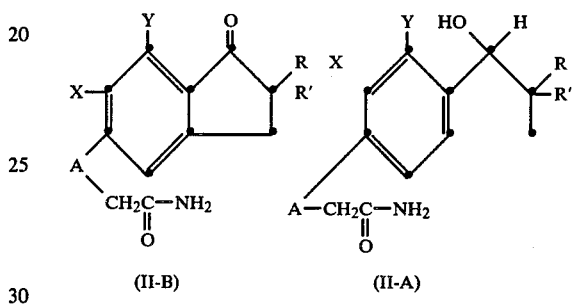

One method for the preparation of the intermediate esters of Formula III is carried out by esterification of the appropriate carboxylic acid of Formula VI.

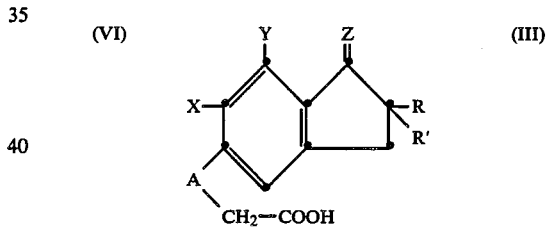

The reaction is conducted using the appropriate alcohol (Alkyl-OH) such as methanol or ethanol, as a solvent and employing a small quantity of an acid catalyst, such as boron trifluoride etherate, sulfuric acid or p-toluenesulfonic acid. The reaction is generally carried out at the boiling point of the alcohol for a period of one to five hours. Another method of preparing esters of Formula III will be described later.

The intermediate acid chlorides of Formula IV are generally generated by methods well-known to those skilled in the art, such as by the reaction of the appropriate acid of Formula VI with a reagent, such as, thionyl chloride in a solvent, such as benzene or toluene at the boiling point of the solvent for a period of one to four hours.

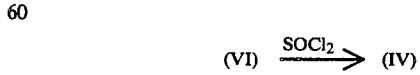

The intermediate acylimidazoles can be prepared by the reaction of the appropriate carboxylic acid of Formula VI with 1,1'-carbonyldiimidazole in a solvent, such as tetrahydrofuran or dioxane at temperatures of −10° to 10° C. for periods of 15 minutes to 2 hours.

The carboxylic acid intermediates of Formula VI where A is O or O(CH$_2$)$_{q'}$ are designated by Formula VI-A. They are prepared by any one of several methods:

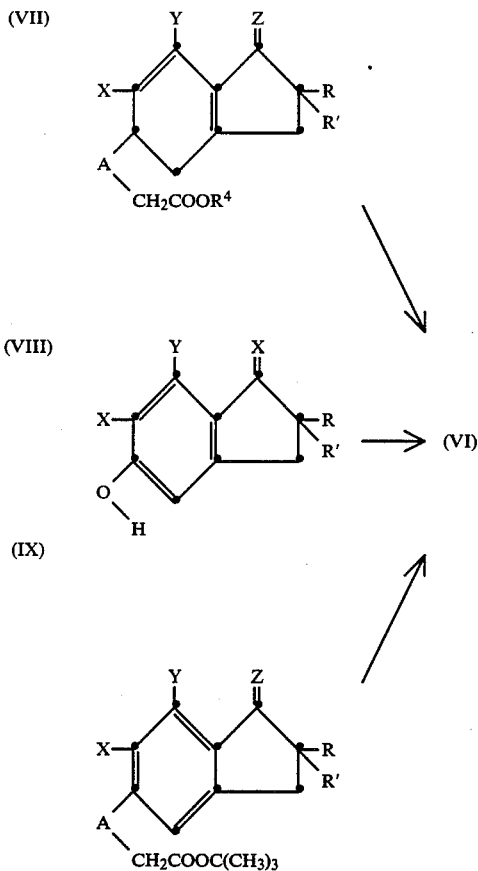

The first method involves heating the ester of Formula VII, where R$^4$=alkyl, in a solution of acetic acid and an aqueous inorganic acid, such as hydrochloric acid, sulfuric acid and the like. The hydrolysis also can be effected in aqueous alcoholic base such as sodium hydroxide or potassium hydroxide in aqueous methanol or ethanol. The product is recovered by acidification with an acid, such as, hydrochloric acid. The reaction can be carried out at temperature of 30° C. to 100° C. for periods of about 20 minutes to 6 hours, depending on the specific ester used and the other reaction conditions. In the instances, where the ester is sensitive to strong base, it is advantageous to carry out the hydrolysis using a weak base, such as aqueous sodium bicarbonate. A solvent, such as aqueous ethanol, methanol or isopropyl alcohol is used and the mixture heated to 45° C. to 100° C. for periods of 15 minutes to 4 hours. Acidification of the reaction mixture with a strong aqueous acid, such as hydrochloric acid, hydrobromic acid or sulfuric acid produces the desired compound of Formula VI.

A second method for the preparation of compounds of the type illustrated by Formula VI involve the reaction of a haloalkanoic or halocycloalkanoic acid (W—A—COOH) with the appropriate phenol of Formula VIII.

Using a haloalkanoic or halocycloalkanoic acid W—A—COOH, where W=iodo, bromo or chloro and A is as defined above, for example, iodoacetic acid or bromofluoroacetic acid, as the etherification agent, the reaction is conducted in the presence of a base. The base is selected from among the alkaline earth or alkali metal bases such as sodium or potassium carbonate, calcium hydroxide and the like. The reaction is carried out in a liquid reaction milieu, the choice being based on the nature of the reactants; however, solvents which are reasonably inert to the reactants and are fairly good solvents for the compounds of Formula VIII and the W—A—COOH reagent, can be used. Highly preferable are dimethylformamide, ethanol, acetone, and N-methyl-2-pyrrolidinone and the like.

A third method for preparing compounds of Formula VI involves the pyrolysis of the corresponding tert.-butyl ester of Formula IX. This method involves heating a tert.-butyl ester of the type illustrated by Formula IX at from about 80° C. to 120° C. in a suitable nonaqueous solvent in the presence of catalytic amount of a strong acid. The solvents are generally selected from among the type benzene, toluene, xylene, etc. and the acid catalyst may be a strong organic or inorganic acid, such as p-toluenesulfonic acid, benzenesulfonic acid, methanesulfonic acid, sulfuric etc. The acid, being a catalyst, is generally used in relatively small quantities as compared to the tert.-butyl ester, IX. It is to be noted that this reaction is a pyrolysis and not a hydrolysis, since water is excluded from the reaction and the products are a carboxylic acid (Formula VI) and isobutylene and no alcohol is produced.

Another method of converting compounds of Type IX to those of Type VI is by heating compounds of Type IX with trifluoroacetic acid in a solvent like dichloromethane.

A fourth method is limited to the instances wherein A=O(CH$_2$)$_2$, which produces compounds of Formula VI-A. In this method, a compound of Formula X is oxidized to a compound of Formula VI-A.

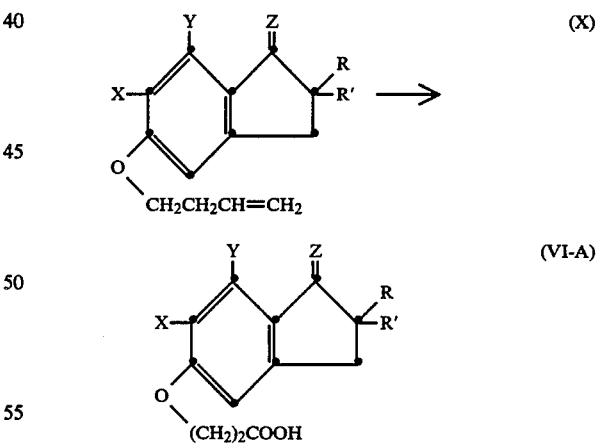

The reaction is conducted in a solvent mixture of water and methylene chloride (or carbon tetrachloride) using an oxidizing agent, such as potassium permanganate and a phase transfer agent, such at "triton B" and the like.

The reaction is conducted conveniently at 10° C., but temperatures as low as 5° C. or as high as 35° C. can be used for periods of 30 minutes to 6 hours.

The product is conveniently isolated by reducing the excess potassium permanganate with sodium bisulfite and hydrochloric acid, extracting the organic phase with aqueous sodium hydroxide and acidifying the aqueous extract with an acid such as hydrochloric acid. If necessary, the product is purified by chromatography or recrystallization.

Compounds of formula X are prepared from the corresponding phenol of Formula VIII by reaction with 1-bromobutene or 1-iodobutene. The reaction (where Hal=bromo or iodo)

VIII+Hal—CH₂CH₂CH=CH₂→X is conveniently conducted in a polar solvent, such as dimethylformamide, 1-methyl-pyrrolidone and the like. A base, such as potassium carbonate or sodium carbonate is employed to scavange the acid that is produced by the reaction. It is often beneficial to heat the base with the phenol (VIII) for a period of 10 minutes to an hour at 90° to 100° C. to generate the salt of the phenol before the 1-bromobutene or 1-iodobutene is added. The final reaction is generally conducted at temperatures of 50° to 100° C. for periods of 12 to 14 hours.

The esters of Formula VII or IX are conveniently prepared by the reaction of a phenol of Formula VIII with a haloalkanoic acid ester of Formula W(CH₂)$_q$COOR⁴. When R⁴ is tert.-butyl, compounds of Formula IX are produced.

VIII+W(CH₂)$_q$COOR⁴→VII or IX

If lower temperatures are employed or if the particular halo ester is not very reactive, the reaction time may be much longer.

In general, the reaction is conducted in the presence of a base, such as an alkali metal carbonate, hydroxide or alkoxide such as potassium carbonate, sodium carbonate, potassium hydroxide, sodium ethoxide and the like. Solvents which are essentially inert to the reactants and product and in which the reactants and product are reasonably soluble are usually employed. Dimethylformamide, ethanol and acetone, for example, have been found to be especially advantageous to use as solvents. The reaction may be conducted at a temperature in the range from about 25° C. to the boiling point temperature of the particular solvent employed. The reaction is generally complete in about 15 to 60 minutes; but, the reaction may require a longer period of time.

The phenols of Formula VIII are prepared by any one of several methods; but the following method is especially convenient. This procedure involves the ether cleavage of anisoles of Formula XI or oxyacetic acids of Formula VI-B. This ether cleavage is:

(XI) 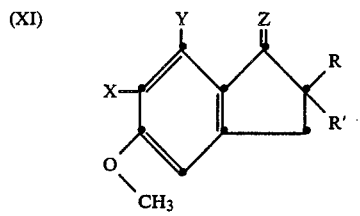 (VIII)

(VI-B) 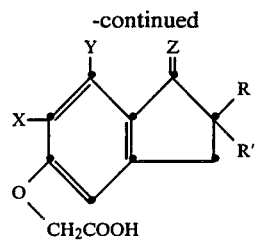

accomplished by any one of many agents known to cleave ethers, especially useful are the hydrohalide salts of weak bases, such as pyridine hydrochloride or pyridine hydrobromide, but other agents, such as aqueous hydrobromic acid, aluminum bromide or sodium nitrite in dimethylformamide can be used. When pyridine hydrohalides are used, the temperatures above that which these substances melt are generally employed. This usually involves temperatures in the range of 150° to 215° C., but temperatures somewhat lower or higher can be used. The period of heating varies depending on the specific compound, but periods of from 15 minutes to 2 hours may be used.

The anisoles of Formula XI are prepared by any one of several methods known to those skilled in the art; however, a convenient method consists in the reaction of a compound of Formula XII with a compound of Formula W—R' where W is as defined previously (iodo, bromo or chloro).

(XII) 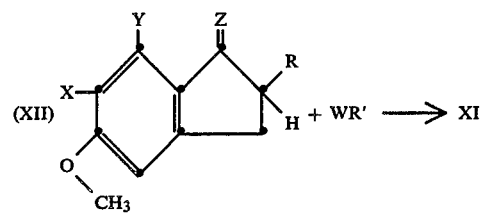

The reaction is generally carried out by first treating the compound of Formula XII with a suitable base, for example, an alkali metal hydride, such as sodium hydride and the like, or an alkali metal alkoxide, for example potassium tert. butoxide and the like. The ion that is generated is then treated with the compound of Formula W—R' (an alkyl halide, alkenyl halide or alkynyl halide). Any solvent which is substantially inert to the reactants employed may be used. Suitable solvents include, for example, 1,2-dimethoxyethane, tert.-butyl alcohol, benzene, toluene, dimethylformamide and the like. The reaction is conducted at temperatures in the range of 25° C. to about 125° C. In general, the reaction is conducted in the range from about 15° to 50° C. It is beneficial to conduct the reaction in a dry, inert atmosphere, for example in dry nitrogen or dry argon.

The carboxylic acid intermediates of Formula VI where A is a bond and Z is O=(designated as VI-B) are prepared by the following sequence of three synthetic steps.

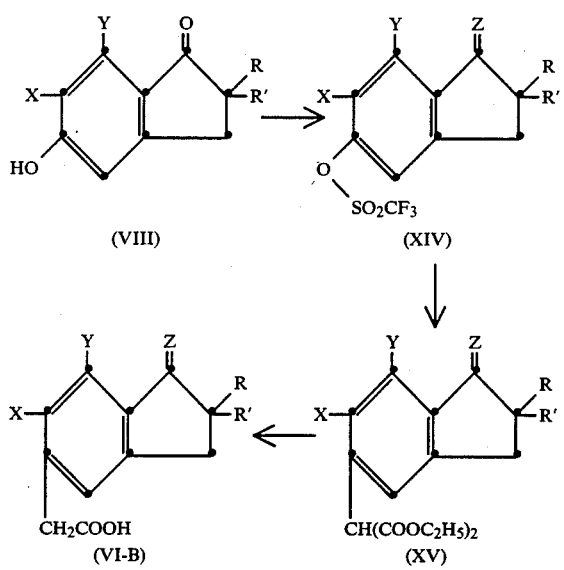

(VIII) → (XIV) → (XV) → (VI-B)

The 2,3-dihydro-1-oxo-1H-inden-yl trifluoromethanesulfonates of Formula XIV are prepared from the corresponding phenols of Formula VIII. The reaction is conducted in a polar solvent, such as dimethylformamide or 1-methyl-2-pyrrolidinone in the presence of a base, such as potassium carbonate or sodium carbonate. The reaction is generally carried out at temperatures in the range of −10° C. to 45° C. but temperatures somewhat higher or lower can be used. The reaction time varies from 30 minutes to 6 hours.

The diethyl(2,3-dihydro-1-oxo-1H-inden-yl)-malonates of Formula XV are prepared by the reaction of compounds of Formula XIV with a metal salt of diethylmalonate. The metal salt of diethyl malonate is conveniently prepared from diethyl malonate and sodium hydride in an inert atmosphere using a solvent, such as dimethylformamide or 1-methyl-2-pyrrolidinone. The metal salt of diethyl malonate in the solvent is then treated with a compound of Formula XIV in an inert organic solvent, for example benzene or toluene. The reaction is generally conducted at a temperature of −5° C. to 50° C. for a period of 6 to 24 hours.

Finally, the compounds of Formula VI-B are prepared by heating compounds of Formula XV with aqueous base. Bases, such as sodium hydroxide or potassium hydroxide are especially useful. To achieve adequate solubility during the reaction, an inert organic solvent is employed, such as ethanol or propanol along with the water. The reaction is generally conducted at temperatures in range of 50° C. to 100° C. for periods of 2 to 24 hours. The final product (VI-B) is generated by acidification of the reaction mixture.

As mentioned earlier, the compounds of this invention possess one and sometimes two asymmetric carbon atoms. In the instances where they possess two asymmetric carbon atoms, the reaction whereby these chiral centers are established can produce two diastereomers. These may be separated to obtain each pure diastereomer by methods well known to those skilled in the art, such as by fractional crystallization, column chromatography, high pressure liquid chromatography and the like.

Those compounds possessing only one asymmetric carbon atom, as well as each pure diastereomer from compounds possessing two asymmetric carbon atoms, consist of a racemate composed of two enantiomers. The resolution of the two enantiomers may be accomplished by forming a salt of the racemic mixture with an optically active base such as (+) or (−)amphetamine, (−)-cinchonidine, dehydroabietylamine, (+) or (−)-α-methylbenzylamine, (+) or (−)(1-naphthyl)ethylamine, (+) cinchonine, brucine, or strychnine and the like in a suitable solvent such as methanol, ethanol, 2-propanol, benzene, acetonitrile, nitromethane, acetone and the like. There is formed in the solution, two diastereomeric salts, one of which is usually less soluble in the solvent than the other. Repetitive recrystallization of the crystalline salt generally affords a pure diastereomeric salt from which is obtained the desired pure enantiomer. The optically pure enantiomer of the compound of Formula I is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

A method which is especially useful in obtaining pure enantiomers involving asymmetry about the 2-carbon atom is to use pure enantiomers of the intermediate compounds. This is particularly advantageous in the instance of compounds of Formula VI, most particularly compound of Formula VI-B. These compounds are readily resolved by the methods described above and many have already been described in the scientific and patent literature. These resolved compounds can then be used per se in subsequent synthetic steps, such as conversion to compounds of the types illustrated by Formula III, IV, V or VII which ultimately lead to compounds of Formula I which are pure enantiomers.

When compounds of Formula I are prepared where both the 1-carbon atom and the 2-carbon atom of the indane ring are asymmetric, the two diastereomers that are produced may be separated by methods well-known to those that are skilled in the art. For example, methods such as fractional crystallization, column chromatography, high pressure liquid chromatography and the like may be used.

The instances where intermediate compounds are used which are preresolved to the pure enantiomers in regard to the 2-carbon atom prior to establishment of the asymmetry about the 1-carbon is established are especially advantageous. An example of this is the reduction of a compound of Formula II-B to one of Formula II-A. In this situation, two diastereomers are produced but each consists of a single enantiomer. Thus, by using one of the methods for separating diastereomers listed above, the two diastereomers can be separated to obtain two pure enantiomers.

Therefore, by starting with a pure enantiomer of Formula VI, two of the possible enantiomers can be obtained. Then, by using the opposite enantiomer of Formula VI the other two enantiomers can be obtained. This provides a method of obtaining all four enantiomers of compounds of Formula I where both the 1-carbon and 2-carbon atoms are asymmetric.

The acid addition salts of Formula I-G (where B+ represents a cation from a pharmaceutically acceptable base) are prepared by reacting a carboxylic acid of Formula I with an appropriate base of formula BH, for example, alkali metal or alkaline earth bicarbonate, carbonate or alkoxide, an amine, ammonia, an organic quaternary ammonium hydroxide, guanidine and the like. The reaction is illustrated below:

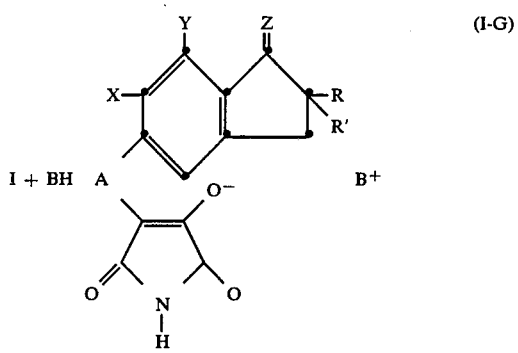

The reaction is generally conducted in water when alkali metal hydroxides are used, but when alkoxides and the organic bases are used, the reaction may be conducted in an organic solvent, such as ether, ethanol, dimethylformamide and the like.

The preferred salts are the sodium, ammonium, diethanolamine, 1-methylpiperazine, piperazine and the like salts.

It is to be recognized that compounds of Formula I are dibasic acids but it is generally intended to prepare only the salts derived from the more acidic center as shown by Formula I-G. Therefore, only bases of the appropriate base strength are used to produce the monobasic salts of Formula I-G or, alternatively, the bases are used only in amounts equivalent to the molar quantities of the acid. In the instance of diacidic bases, for example 1-methylpiperazine, molecular equivalent amounts of compounds of Formula I and BH are used.

Inasmuch as there are a variety of symptoms and severity associated with grey matter edema, particularly when it is caused by head trauma stoke, cerebral hemorrhage or embolism, post-operative brain surgery trauma, spinal cord injury, cerebral infections and various brain concussions, the precise treatment is left to the practitioner. Therefore, it is left to the judgment of the practitioner to determine the patient's response to treatment and to vary the dosages accordingly. A recommended dosage range is from 1 microgram/kg to 20 mg/kg of body weight as a primary dose and a sustaining dose of half to equal the primary dose, every 4 to 24 hours.

The compounds of this invention can be administered by a variety of established methods, including intravenously, intramuscularly, subcutaneously, or orally. As with dosage, the precise mode of administration is left to the discretion of the practitioner. However, for the very ill and comatose patient, the parenteral route, particularly the intravenous route of administration is highly preferred. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type Formula I in the form of their salts (Formula I-G) is superior.

One aspect of this invention is the treatment of persons with grey matter edema by concomitant administration of a compound of Formula I or I-G, a pharmaceutically acceptable salt, and an antiinflammatory steroid. These steroids are of some, albeit limited, use in control of white matter edema associated with ischemic stroke and head injury. Steroid therapy is given according to established practice as a supplement to the compound of Formula I or I-G as taught elsewhere herein.

Similarly, a barbiturate may be administered as a supplement to treatment with a compound of Formula I or I-G.

The compounds of Formula I or I-G are utilized by formulating them in a composition such as tablet, capsule or elixir for oral administration. Sterile solutions or suspensions can be used for parenteral administration. About 70 micrograms to 750 mg of a compound or mixture of compounds of Formula I or I-G, its a physiologically acceptable salt, is compounded with a physiologically acceptable vehicle, carrier, excipient, binder, preservative, stabilizer, flavor, etc. in a dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit from is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water by injection, a naturally occurring vegetable oil like sesame oil, coconut oil, peanut oil, cottonseed oil, etc., or a synthetic fatty vehicle like ethyl oleate or the like. Buffer, preservatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. Aug. 29–31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglia as a secondary, inhibitable process. At the molecular level, the sequence appears to be: trauma, elevation of extracellular $K^+$ and/or release of neuro-transmitters, edema, hypoxia and necrosis. Astroglial swelling results directly from a $K^+$-dependent, cation-coupled, chloride transport from the extracellular into the intracellular compartment with a concommitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I and I-G exhibit the desired effects on brain edema and are relative free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound ethacrynic acid) which exhibited activity both in vitro and in vivo assays was effective in reducing mortality in clinical cases of head injury. These studies are described in the Journal of Medicinal Chemistry, Volume 18, page 567 (1982).

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. in "Seminars in Neurological Surgery: Neural Trauma"; Popp, A. J.; Bourke, R. S.; Nelson, L. R.; Kimelberg, H. K,. Eds.; Raven Press; New York, 1979; p. 347, by Bourke, R. S.; Kimelberg, H. K.; Daze, M. A. in Brain Res. 1978, 154, 196, and by Bourke, R. S.; Kimelberg, H. K.; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, c.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V.; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the assays described supra, compounds of this invention exhibit marked activity both in vitro and in vivo. For example, in the in vitro assays compounds of Formula I and I-G inhibit chloride transport by 50% at concentrations as low as $10^{-9}$ to $10^{-10}$ molar and lower. Likewise in the in vivo assay compound of Formula I or I-G reduce the mortality due to head injury by statistically significant values as compared to control animals.

The following examples are included to illustrate the preparation of representative compounds of Formula I and I-G and representative dosage forms of these compounds.

EXAMPLE 1

(+)3-(6,7-Dichloro-2-cyclopentyl-2,3-dihydro-2-methyl-1-oxo-1H-inden-5-yl)-4-hydroxy-1H-pyrrole-2,5-dione and its 1-Methylpiperazine Salt

Step A:

(+)3-(6,7-Dichloro-2-cyclopentyl-2,3-dihydro-2-methyl-1-oxo-1H-inden-5-yl) Trifluoromethane-sulfonate A mixture of (+)-6,7-dichloro-2-cyclopentyl-2,3-dihydro-5-hydroxy-2-methyl-1H-inden-1-one (25.05 g, 0.0837 mole) and potassium carbonate (35.4 g. 0.256 mole) in dimethylformamide (100 ml.) is stirred at 25° C. for 1 hour, cooled to 0° C. then treated with trifluoromethanesulfonyl chloride (10.5 ml., 0.984 mole) over a 3 minute period. The reaction mixture is stirred at 25° C. for 1 hour, poured into ice water (700 ml.) extracted with ether, washed with water and brined and dried over MgSO$_4$. The ether is evaporated at reduced pressure to give 34.2 g of (+) (+)-(6,7-dichloro-2-cyclopentyl-2,3-dihydro-2-methyl-1-oxo-1H-inden-5-yl) trifluoromethanesulfonate which melts at 104°-6° C. and is used in Step B without further purification.

Step B:

(+)-(6,7-Dichloro-2-cyclopentyl-2,3-dihydro-2-methyl-1-oxo-1H-inden-5-yl)acetic Acid Diethyl malonate (34.4 g., 0.215 mole) is added to a stirred suspension of sodium hydride (56% on mineral oil, 9.2 g., 0.215 mole) in dimethylformamide (130 ml.) at 10°-15° C. in an inert atmosphere during a 1 hour period. The reaction mixture is stirred at 25° C. for 1.5 hours, cooled to 5° C. and treated with (+)-(6,7-dichloro-2-cyclopentyl-2,3-dihydro-2-methyl-1-oxo-1H-inden-5-yl) trifluoromethanesulfonate 34.2 g., 0.0793 mole) in toluene (45 ml.) over a 1 hour period 5°-7° C. The reaction mixture is stirred at 25° C. for 18 hours, poured into a mixture of ice water (700 ml.) and concentrated hydrochloric acid (20 ml.), extracted with ether (3×125 ml.) and methylene chloride (125 ml.). The combined organic extracts were washed with water and brine and dried over MgSO$_4$.

Evaporation of the organic solvents at reduced pressure gives crude (+)-diethyl (6,7-dichloro-2-cyclopentyl-2,3-dihydro-2-methyl-1-oxo-1H-inden-5-yl)malonate which is dissolved in ethanol (100 ml), treated with a solution of sodium hydroxide (40 g) in water (300 ml.) and heated at reflux for 4 hours. The reaction mixture is cooled, diluted with water (300 ml) and extracted with hexane (2×125 ml).

The aqueous layer is acidified with hydrochloric acid, extracted with ether (4×100 ml) then extracted into aqueous sodium bicarbonate (15×100 ml) which is acidified with hydrochloric acid and extracted with ether and methylene chloride. The combined organic extracts are washed with water and brine, dried over MgSO$_4$ and evaporated at reduced pressure to give 23 g. of (+)-(6,7-dichloro-2-cyclopentyl-2,3-dihydro-2-methyl-1-oxo-1H-inden-5-yl)acetic acid. A small sample is converted to its dicyclohexylamine salt, m.p., 163° C.

Analysis for $C_{17}H_{18}Cl_2O_3 \cdot C_{12}H_{23}N$; Calc. C, 66.66; H, 7.91; N, 2.68; Found: C, 66.15; H, 8.17; N, 2.71%.

Step C:
(+)-(6,7-Dichloro-2-cyclopentyl-2,3-dihydro-2-methyl-1-oxo-1H-inden-5-yl)acetamide To a solution of (+)-(6,7-dichloro-2-cyclopentyl-2,3-dihydro-2-methyl-1-oxo-1H-inden-5-yl)acetic acid (21.8 g., 0.0623 mole) in chloroform (150 ml) and dimethylformamide (1 drop) is added thionyl chloride (25 ml). The reaction mixture is heated at reflux for 3 hours, cooled and concentrated at reduced pressure. The crude (+)-(6,7-dichloro-2-cyclopentyl-2,3-dihydro-2-methyl-1-oxo-1H-inden-5-yl)acetyl chloride, thus obtained, is dissolved in methylene chloride (75 ml) and added over 0.5 hour to a mixture of ether (100) ml) and methylene chloride (75 ml) which has been saturated with ammonia.

The addition is conducted at 0°–10° C. Ammonia is passed into the solution for 15 minutes following the addition and then concentrated aqueous ammonia (25 ml) and water (150 ml) are added. The organic layer is washed with water, brine, dried over MgSO$_4$ and evaporated at reduced pressure leaving 19.8 g. of (+)-(6,7-dichloro-2-cyclopentyl-2,3-dihydro-2-methyl-1-oxo-1H-inden-5-yl)acetamide as a foam which is used in Step D without further purification.

Step D:
(+)3-(6,7-Dichloro-2-cyclopentyl-2,3-dihydro-2-methyl-1-oxo-1H-inden-5-yl)-4-hydroxy-1H-pyrrole-2,5-dione and its 1-Methylpiperazine salt In a nitrogen atmosphere, (+)-(6,7-dichloro-2-cyclopentyl-2,3-dihydro-2-methyl-1-oxo-1H-inden-5-yl)acetamide (19.8 g., 0.0582 mole) and diethyl oxalate (9.14 g., 0.0626 mole) are dissolved in dimethylformamide (100 ml.) and stirred in an ice bath. Potassium tert. butoxide (15.2 g, 0.136 mole) is added in two portions at a 10 minute interval. The reaction mixture is stirred at 25° C. for 18 hours, poured into water (600 ml) acidified with hydrochloric acid, extracted with ether, washed with water and brine and dried over MgSO$_4$. Evaporation of the ether at reduced pressure gives (+)3-(6,7-dichloro-2-cyclopentyl-2,3-dihydro-2-methyl-1-oxo-1H-inden-5-yl)-4-hydroxy-1H-pyrrole-2,5-dione as the hemietherate in the form of a foam. Upon drying at reduced pressure, the analysis of the hemietherate is as follows:

Calc. for $C_{19}H_{17}Cl_2NO_4 \cdot \frac{1}{2}C_4H_{10}O$: C, 58.48; N, 5.14; N, 3.25; Found: C, 58.61; H, 4.91; N, 3.45%.

Further drying of the hemietherate at reduced pressure at about 70° C. gives the solvent free material.

The 1-methylpiperazine salt of the above described compound is prepared by dissolving the compound in ether and treating it with an equimolar quantity of 1-methylpiperazine which gives a precipitate which upon filtration and drying weighs 25.2 g. After recrystallization from 2-propanol this salt melts at 204°–206° C., $[\alpha]^{25}D = +21.7°$ (C=1, CH$_3$OH).

Analysis, calculated for $C_{19}H_{17}Cl_2NO_4 \cdot C_5H_{12}N_2$; C, 58.30; H, 5.91; N, 8.50; Found: C, 58.05; H, 5.98; N, 8.67%.

EXAMPLE 2

(+)3-(6,7-Dichloro-2-cyclopentyl-2-ethyl-2,3-dihydro-1-oxo-1H-inden-5-yl)-4-hydroxy-1H-pyrrole-2,5-dione and its 1-Methylpiperazine salt The preparation is conducted essentially as described in Example 1, Steps A through D except that an equimolar amoount of 6,7-dichloro-2-cyclopentyl-2-ethyl-2,3-dihydro-5-hydroxy-1H-inden-1-one is substituted for the (+)-6,7-dichloro-2-cyclopentyl-2,3-dihydro-5-hydroxy-2-methyl-1H-inden-1-one used in Example 1, Step A. Then, the product of Steps A, B and C are used in each subsequent step so that 3-(6,7-dichloro-2-cyclopentyl-2-ethyl-2,3-dihydro-1-oxo-1H-inden-5-yl)-4-hydroxy-1H-pyrrole-2,5-dione and its 1-methylpiperazine salt are obtained in Step D.

EXAMPLE 3

3-(2-Butyl-6,7-dichloro-2-cyclopentyl-2,3-dihydro-1-oxo-1H-inden-5-yl)-4-hydroxy-1H-pyrrole-2,5-dione and its 1-Methylpiperazine Salt By following substantially the procedure described in Example 1, Steps A to D, but substituting an equimolar amount of 2-butyl-6,7-dichloro-2-cyclopentyl-2,3-dihydro-5-hydroxy-1H-inden-1-one for the (+)-6,7-dichloro-2-cyclopentyl-2,3-dihydro-5-hydroxy-2-methyl-1H-inden-1-one used in Example 1, Step A and using the product of each step in the subsequent step there are obtained 3-(2-butyl-6,7-dichloro-2-cyclopentyl-2,3-dihydro-1-oxo-1H-inden-5-yl)-4-hydroxy-1H-pyrrole-2,5-dione and its 1-methylpiperazine salt.

Analysis for $C_{22}H_{23}Cl_2NO_4$; Calc. C, 60.55; H, 5.31; N, 3.23; Found: C, 60.56; H, 5.60; N, 3.10%.

EXAMPLE 4

3-(6,7-Dichloro-2,3-dihydro-2-methyl-2-(1-methylethyl)-1-oxo-1H-inden-5-yl)-4-hydroxy-1H-pyrrole-2,5-dione and its 1-Methylpiperazine Salt The preparation is conducted essentially as described in Example 1, Steps A through D except that an equimolecular amount of 6,7-dichloro-2,3-dihydro-5-hydroxy-2-methyl-2-(1-methylethyl)-1H-inden-1-one is substituted for the (+)-6,7-dichloro-2-cyclopentyl-2,3-dihydro-5-hydroxy-2-methyl-1H-inden-1-one used in Example 1, Step A. Then the product of Steps A, B and C are used in each subsequent step so that 3-(6,7-dichloro-2,3-dihydro-1-oxo-methyl-2-(1-methylethyl)-1H-inden-5-yl)-4-hydroxy-1H-pyrrole-2,5-dione and its 1-methylpiperazine salt are obtained in Step D.

EXAMPLE 5

3-(6,7-Dichloro-2-cyclopentylmethyl-2,3-dihydro-2-methyl-1-oxo-1H-inden-5-yl)-4-hydroxy-1H-pyrrole-2,5-dione

Step A:
6,7-Dichloro-2-cyclopentylmethyl-2,3-dihydro-5-methoxy-2-methyl-1H-inden-1-one 6,7-Dichloro-2-cyclopentylmethyl-2,3-dihydro-5-methoxy-1H-inden-1-one (56.7 g., 0.181 mole) dissolved in dry toluene (200 ml.) is added dropwise with stirring under nitrogen over 1 hour at room temperature to a suspension of sodium hydride (56% in mineral oil, 8.74 g. 0.204 mole) in toluene (50 ml) and dry dimethylformamide (220 ml.) The mixture is stirred at room temperature for 1.75 hours after completion of the addition, cooled to 0° C., and then methyl iodide (25 ml., 0.4 mole) is added at 0°–5° C. After stirring at 5° for 25 minutes and for one hour at room temperature, methanol (15 ml.) is slowly added followed by acetic acid (10 ml.). The mixture is poured into ice water (1500 ml.) the layers are separated and the aqueous phase extracted three times with toluene (150 ml.) and then with methylene chloride (150 ml.). The combined organic extracts are washed with water, dried over magnesium sulfate and concentrated under vacuum. The residue is triturated with a mixture of hexane and petroleum ether (1:1) are filtered. The solid (50 g.) is recrystallized from a mixture of methylcyclohexane (110 ml.) and hexane (55 ml.) to obtain 38 g. of product, m.p. 75°–77° C. The filtrates from the recrystallization are concentrated and the residue recrystallized from methylcyclohexane to obtain a second drop of 5.5 g. for a total yield of 73%.

Step B:
6,7-Dichloro-2-cyclopentylmethyl-2,3-dihydro-5-hydroxy-2-methyl-1H-inden-1-one 6,7-Dichloro-2-cyclopentylmethyl-2,3-dihydro-5-methoxy-2-methyl-1H-inden-1-one (43.5 g., 0.1329 mole) is added to fused pyridine hydrochloride (440 g.) at 160° C. the mixture is heated with stirring under nitrogen at an internal temperature of 175°–185° C. for 80 minutes. The molten mixture is poured into ice and water (1500 ml.). The solid is extracted with methylene chloride and then ether. The combined organic extracts are washed with water, dried over magnesium sulfate and concentrated in vacuo. The filtrate is further concentrated to obtain an additional 7.0 g. of 6,7-dichloro-2-cyclopentylmethyl-2,3-dihydro-5-hydroxy-2-methyl-1H-inden-1-one, m.p., 188°–90° for a total yield of 96%.

Step C:
(6,7-Dichloro-2-cyclopentylmethyl-2,3-dihydro-2-methyl-1-oxo-1H-inden-5-yl) Trifluoromethanesulfonate Anhydrous potassium carbonate (17.7 g., 0.128 mole) is added to a solution of 6,7-dichloro-2-cyclopentylmethyl-2,3-dihydro-5-hydroxy-2-methyl-1H-inden-1-one (13.35 g., 0.0426 mole) in dry dimethylformamide (60 ml.) The suspension is stirred for 1 hour at room temperature, cooled to 15° C. and then trifluoromethanesulfonyl chloride is added at 15°–18° C. After stirring for 1 hour at room temperature, the reaction mixture is poured into ice water (700 ml.). The oil that separates is extracted with ether (125 ml.). The combined organic extracts are washed with water, dried over magnesium sulfate and concentrated in vacuo to obtain the amber, oily product (18.8 g.), which is used in the next step without further purification.

Step D:
(6,7-Dichloro-2-cyclopentylmethyl-2,3-dihydro-2-methyl-1-oxo-1H-inden-5-yl)acetic acid Diethyl malonate (18.3 g., 0.114 mole) is added with stirring under nitrogen at 10°–15° C. to a suspension of sodium hydride (56% in mineral oil, 4.89 g., 0.114 mole) in dry dimethylformamide (85 ml.). The reaction mixture is stirred for 1 hour at room temperature, cooled to 5° C. and then 6,7-dichloro-2-cyclopentylmethyl-2,3-dihydro-2-methyl-1-oxo-1H-inden-5-yl trifluoromethanesulfonate (18.8 g., 0.0426 mole dissolved in dry toluene (20 ml.) is added over 1 hour at 5°–7° C. After stirring at room temperature for 18 hours, the reaction mixture is poured into ice water (1000 ml.) and extracted with ether (4×150 ml.) and then with methylene chloride (2×50 ml.). The combined organic extracts are washed three times with water and concentrated under vacuum. The residual oil is dissolved in ethanol (150 ml.) and added to a solution of 20 g. of sodium hydroxide in water (150 ml.). The mixture is refluxed for 3 hours, cooled and the ethanol removed under vacuum. The residue is diluted with water, extracted with hexane and then acidified with hydrochloric acid. The gum that separates is extracted with ether. The combined etheral extracts are washed with water and then extracted repeatedly with dilute sodium bicarbonate. The combined aqueous extracts are acidified with hydrochloric acid and extracted with ether. The ether extracts are washed with brine, dried over magnesium sulfate an concentrated under vacuum to obtain the crude (6,7-dichloro-2-cyclopentylmethyl-2,3-dihydro-2-methyl-1-oxo-1H-inden-5-yl)acetic acid, 9.3 g., m.p. 145.5°–148° C., in 62% yield. Recrystallization from butyl chloride affords material which melts at 149°–151° C.

Calc. for $C_{18}H_{20}Cl_{20}Cl_2O_3$: C, 60.85; H, 5.67; Found: C, 60.86; H, 6.02;

Step E:
(6,7-Dichloro-2-cyclopentylmethyl-2,3-dihydro-2-methyl-1-oxo-1H-inden-yl)acetamide To (6,7-Dichloro-2-cyclopentylmethyl-2,3-dihydro-2-methyl-1-oxo-1H-inden-5-yl)acetic acid (5.68 g., 0.016 mole) dissolved in chloroform (25 ml.) containing dimethylformamide (1 drop), thionyl chloride 92.4 ml., 0.33 mole) is added. The mixture is refluxed for 16 hours, cooled, concentrated under vacuum and the residual acid chloride dissolved in methylene chloride (25 ml.). The solution is added over 10 minutes with stirring and cooling in an ice bath to a solution of ether (200 ml.) which had been saturated with ammonia. The mixture is stirred an additional 10 minutes and then poured into ice water. The layers are separated and the aqueous phase extracted with ether and then with methylene chloride. The combined organic extracts are washed with brine, dried over magnesium sulfate and concentrated under vacuum to obtain the (6,7-dichloro-2-cyclopentylmethyl-2,3-dihydro-2-methyl-1-oxo-1H-inden-5-yl)acetamide, 5.0 g., 88%, as an orange colored foam which is used in the next step without further purification.

Step F:
3-(6,7-Dichloro-2-cyclopentylmethyl-2,3-dihydro-2-methyl-1-oxo-1H-inden-5-yl)-4-hydroxy-1H-pyrrole-2,5-dione (6,7-Dichloro-2-cyclopentylmethyl-2,3-dihydro-2-methyl-1-oxo-1H-inden-5-yl)acetamide (5 g., 0.0141 mole) and diethyl oxalate (2.19 g., 0.015 mole) are dissolved in dry dimethylformamide (30 ml.) and stirred in an ice bath under nitrogen for 20 minutes. Potassium t-butoxide (3.53 g., 0.0315 mole) is then added in two portions 15 minutes apart. The mixture is stirred while cooling in the ice bath for another 45 minutes, then stirred at room temperature for 18 hours and poured into ice water (500 ml.) The mixture is acidified with hydrochloric acid and extracted with ether (4×125 ml.). The combined organic extracts are washed with water and then repeatedly extracted with dilute sodium carbonate. The combined aqueous extracts are acidified with hydrochloric acid, extracted with methylene chloride and then with ether. The combined organic extracts are washed with water, dried over magnesium sulfate and concentrated under vacuum. The residue is chromatographed on silica (175 g.) with a mixture of toluene, dioxane and acetic acid (50:5:1). The appropriate product fractions are concentrated under vacuum and the residue is dissolved in ether and extracted with dilute sodium bicarbonate. The aqueous extracts are acidified with hydrochloric acid and extracted with methylene chloride and then with ether. The combined organic extracts are washed with water, dried over magnesium sulfate and concentrated under vacuum to obtain the 3-(6,7-Dichloro-2-cyclopentylmethyl-2,3-dihydro-2-methyl-1-oxo-1H-inden-5-yl)-4-hydroxy-1H-pyrrole-2,5-dione as a foam which was then dried under high vacuum at 90° C. for 2 hours to give 3.6 g. (63%).

Calculated for $C_{20}H_{10}Cl_2NO_4$: C, 58.85; H, 4.69; N, 3.43; Found: C, 58.90; H, 4.98; N, 3.20;

EXAMPLE 6
3-(2-Allyl-6,7-dichloro-2,3-dihydro-2-methyl-1-oxo-1H-inden-5-yl)-4-hydroxy-1H-pyrrole-2,5-dione and its 1-Methylpiperazine Salt The preparation is carried out essentially as described in Example 1, Steps A through D, except that an equimolar amount of 2-allyl-6,7-dichloro-2,3-dihydro-5-hydroxy-2-methyl-1H-inden-1-one is substituted for the (+)-6,7-dichloro-2-cyclopentyl-2,3-dihydro-5-hydroxy-2-methyl-1H-inden-1-one used in Example 1, Step A. Then, the product of Steps A, B and C are used in each subsequent step so that 3-(2-allyl-6,7-dichloro-2,3-dihydro-2-methyl-1-oxo-1H-inden-5-yl)-4-hydroxy-1H-pyrrole-2,5-dione and its 1-methylpiperazine salt is obtained in Step D.

EXAMPLE 7
3-(6,7-dichloro-2,3-dihydro-1-oxo-phenyl-2-propargyl-1H-inden-5-yl)-4-hydroxy-1H-pyrrole-2,5-dione and its 1-Methylpiperazine Salt

Step A:
6,7-dichloro-2,3-dihydro-5-hydroxy-2-phenyl-2-propargyl-1H-inden-1-one The preparation is conducted essentially as described in Example 5, Step B except that an equimolar amount of [(6,7-dichloro-2,3-dihydro-1-oxo-2-phenyl-2-propargyl-1H-inden-5-yl)oxy]acetic acid is used in place of the 6,7-dichloro-2-cyclopentylmethyl-2,3-dihydro-5-methoxy-2-methyl-1H-inden-1-one used in Example 5, Step B. There is thus obtained 6,7-dichloro-2,3-dihydro-5-hydroxy-2-phenyl-2-propargyl-1H-inden-1-one.

Steps B, C, D and E:
3-(6,7-dichloro-2,3-dihydro-1-oxo-2-phenyl-2-propargyl-1H-inden-5-yl)-4-hydroxy-1H-pyrrole-2,5-dione and its 1-Methylpiperazine Salt The synthesis was carried out essentially as described in Example 1, Steps A through D except that an equimolar amount of 6,7-dichloro-2,3-dihydro-5-hydroxy-2-phenyl-2-propargyl-1H-inden-1-one was used in place of the (+)-6,7-dichloro-2-cyclopentyl-2,3-dihydro-5-hydroxy-2-methyl-1H-inden-1-one used in Example 1, Step A. Then the products of Steps B, C and D are used in each subsequent step so that 3-(6,7-dichloro-2,3-dihydro-1-oxo-2-phenyl-2-progargyl-1H-inden-5-yl)-4-hydroxy-1H-pyrrole-2,5-dione 1-methyl-piperazine salt is obtained in Step E.

EXAMPLE 8
3-(6,7-Dichloro-2,3-dihydro-2-methyl-1-oxo-2-phenyl-1H-inden-5-yl)-4-hydroxy-1H-pyrrole-2,5-dione 1-Methylethanolate The preparation is carried out by following substantially the procedures described in Example 1, Steps A through D, except that an equimolar amount of 6,7-dichloro-2,3-dihydro-5-hydroxy-2-methyl-2-phenyl-1H-inden-1-one is substituted for the (+)-6,7-dichloro-2-cyclopentyl-2,3-dihydro-5-hydroxy-2-methyl-1H-indene-1-one used in Example 1, Step A. Then, the product of Steps A, B and C are used in each subsequent step so that 3-(6,7-dichloro-2,3-dihydro-2-methyl-1-oxo-2-phenyl-1H-inden-5-yl)-4-hydroxy-1H-pyrrole-2,5-dione 1-methylethanolate is obtained in Step D. This product melts at 140°–144° C. after recrystallization from 1-methylethanol.

Analysis Calculated for $C_{20}H_{13}Cl_2NO_4 \cdot C_3H_8O$: N, 3.03; H, 4.58; Cl, 15.34; Found: N, 3.02; H, 4.46, Cl, 15.26%.

EXAMPLE 9
3-(2-Benzyl-6,7-dichloro-2,3-dihydro-2-methyl-1-oxo-1H-inden-5-yl)-4-hydroxy-1H-pyrrole-2,5-dione and its 1-Methylpiperazine Salt Hemietherate The preparation is carried out by following substantially the procedures described in Example 1, Steps A through D, except that an equimolar amount of 2-benzyl-6,7-dichloro-2,3-dihydro-5-hydroxy-2-methyl-1H-inden-1-one is substituted for the (+)-6,7-dichloro-2-cyclopentyl-2,3-dihydro-5hydroxy-2-methyl-1H-inden-1-one used in Example 1, Step A. Then, the product of Steps A, B and C are used in each subsequent step so that 3-(2-benzyl-6,7-dichloro-2,3-dihydro-2-methyl-1-oxo-1H-inden-5-yl)-4-hydroxy-1H-pyrrole-2,5-dione and its 1-methylpiperazine salt hemietherate are obtained in Step D.

Analysis calculated for $C_{21}H_{15}Cl_2NO_4 \cdot C_5H_{12}N_2 \cdot \frac{1}{2}C_4H_{10}O$: C, 60.76; H, 5.83; N, 7.59; Found: C, 60.54; H, 6.00; N. 7.56%.

EXAMPLE 10

3-(6,7-Dichloro-2-p-fluorophenyl-2,3-dihydro-1-oxo-1H-inden-5-yl)-4-hydroxy-1H-pyrrole-2,5-dione and its 1-Methylpiperazine salt The preparation is carried out by following substantially the procedures described in Example 1, Steps A through D, except that an equimolar amount of 6,7-dichloro-2-p-fluorophenyl-2,3-dihydro-5-hydroxy-2-methyl-1H-inden-1-one is substituted for the (+)-6,7-dichloro-2-cyclopentyl-2,3-dihydro-5-hydroxy-2-methyl-1H-inden-1-one that is used in Example 1, and Step A. Then, the product of Steps A, B and C are used in each subsequent step so that 3-(6,7-dichloro-2-p-fluorophenyl-2,3-dihydro-1-oxo-1H-inden-5-yl)-4-hydroxy-1H-pyrrole-2,5-dione and its 1-methylpiperazine salt are obtained in Step D.

EXAMPLE 11

3-(6,7-Dichloro-2,3-dihydro-2-p-methoxyphenyl-2-methyl-1-oxo-1H-inden-5-yl)-4-hydroxy-1H-pyrrole-2,5-dione and its 1-Methylpiperazine salt The preparation is carried out by following substantially the procedures described in Example 1, Steps A through D, except that an equimolar amount of (6,7-Dichloro-2,3-dihydro-2-p-methoxyphenyl-2-methyl-1-oxo-1H-inden-1-one is substituted for the (+)-6,7-dichloro-2-cyclopentyl-2,3-dihydro-5-hydroxy-2-methyl-1H-inden-1-one that is used in Example 1, Step A. Then, the product of Steps A, B and C are used in each subsequent step (i.e. Steps B, C and D respectively) so that 3-(6,7-dichloro-2,3-dihydro-2-p-methoxyphenyl-2-dimethyl-1-oxo-1H-inden-5-yl)-4-hydroxy-1H-pyrrole-2,5-dione and its 1-methylpiperazine salt are obtained in Step D.

EXAMPLE 12

3-[6,7-Dichloro-2,3-dihydro-1-oxo-2-methyl-2-(2-thienyl)-1H-inden-5-yl]-4-hydroxy-1H-pyrrole-2,5-dione and its 1-Methylpiperazine Salt The preparation is carried out by following essentially the procedures described in Example 1, Steps a through D, except that an equimolar amount of 6,7-dichloro-2,3-dihydro-5-hydroxy-2-methyl-2-(2-thienyl)-1H-inden-1-one is substituted for the (+)-6,7-dichloro-2-cyclopentyl-2,3-dihydro-5-hydroxy-2-methyl-1H-inden-1-one that is used in Example 1, Step A. Then, the product of Steps A, B and C are used in each subsequent step (i.e. Steps B, C and D respectively) so that 3-[6,7-dichloro-2,3-dihydro-1-oxo-2-methyl-2-(2-thienyl)-1H-inden-5-yl]-4-hydroxy-1H-pyrrole-2,5-dione and its 1-methylpiperazine salt are obtained in Step D.

EXAMPLE 13

3-[(6,7-Dichloro-2-cyclopentyl-2,3-dihydro-2-methyl-1-oxo-1H-inden-5-yl)oxy]-4-hydroxy-1H-pyrrole-2,5-dione Hemitoluene Solvate and Their (+)-Diastereomers A stirred solution of a mixture of the diastereomeric racemates of 3-[(6,7-dichloro-2-cyclopentyl-2,3-dihydro-1-hydroxy-2-methyl-1H-indenyl)oxy]-4-hydroxy-1H-pyrrole-2,5-dione (2.55 g., 0.0062 mole) in acetone (75 ml.) is treated with a solution of Jones reagent (prepared from $CrO_3$ (0.91 g.) $H_2O$ (6.5 ml.) and $H_2SO_4$ (0.8, $SO_4$ (0.8 ml.)) over a 10 minute period. The acetone solution is decanted from the precipitated salts, evaporated at reduced pressure, poured into water (100 ml.) and extracted with ether which, in turn, is washed with water, dried over $MgSO_4$ and evaporated at reduced pressure. The resultant oil is chromatographed on silica (75 g.) eluted with a mixture of methylene chloride, tetrahydrofuran and acetic acid (50:1:1). The pertinent fractions are evaporated at reduced pressure, the residue treated with toluene (100 ml.) and evaporated to azerotrope the residual acetic acid to provide 3-[(6,7-dichloro-2-cyclopentyl-2,3-dihydro-2-methyl-1-oxo-1H-inden-5-yl)oxy]-4-hydroxy-1H-pyrrole-2,5-dione hemitoluene solvent which melts at 181°3° C.

Analysis calculated for $C_{19}H_{17}Cl_2NO_5.1/2C_7H_8$: N, 3.07; H, 4.64; Cl, 15.54; Found: N, 2.96; H, 4.78; Cl, 15.47%.

By starting with a mixture of the two (+)-diastereomers of 3-[(6,7-dichloro-2-cyclopentyl-2,3-dihydro-1-hydroxy-2-methyl-1H-inden-5-yl)oxy]-4-hydroxy-1H-pyrrole-2,5-dione instead of the mixture of racemates described above there is obtained (+)3-[(6,7-dichloro-2-cyclopentyl-2,3-dihydro-2-methyl-1-oxo-1H-inden-5-yl)oxy]-4-hydroxy-1H-pyrrole-2,5-dione.

EXAMPLE 14

3[(6,7-dichloro-2-cyclopentyl-2,3-dihydro-2-methyl-1-oxo-1H-inden-5-yl)oxymethyl]-4-hydroxy-1H-pyrrole-2,5-dione 1-Methylpiperzine Salt

Step A:

4-[(6,7-Dichloro-2-cyclopentyl-2,3-dihydro-2-methyl-1-oxo-1H-inden-5-yl)oxy]-1-butene 2-Cyclopentyl-6,7-dichloro-2,3-dihydro-2-methyl-5-hydroxy-1H-inden-1-one (12 gm., 0.04 mole) is dissolved in dimethylformamide (30 m.) and treated with potassium carbonate (5.5 gm., 0.04 mole). The mixture is stirred and heated on a steam bath for 30 minutes and 4-bromo-1-butene (5.5 gm., 0.04 mole) is added and the mixture stirred and heated at 60° C. for 24 hours. The reaction mixture is poured into water (300 ml.) and, after standing, the product removed by filtration, dried and recrystallized from petroleum ether. The yield is 11.5 gm., m.p. 63°–65° C.

Analysis Calc. $C_{19}H_{22}Cl_2O_4$: C, 64.59; H, 6.28: Found: C, 64.72; H, 6.46%.

Step B:

4-[(6,7-Dichloro-2-cyclopentyl-2,3-dihydro-2-methyl-1-oxo-1H-inden-5-yl)oxy]propanoic acid A mixture of 4-[(2-cyclopentyl-6,7-dichloro-2,3-dihydro-2-methyl-1-oxo-1H-inden-5-yl)oxy]-1-butene 8.8 gm., 0.025 mole), water (200 ml.), methylene chloride (100 ml.), potassium permanganate (9.9 gm, 0.062 mole) and "triton B" (300 mg.) is stirred at 10° C. for 2 hours. Sodium bisulfite and concentrated hydrochloric acid is added portionwise alternately until a clear solution results. The methylene chloride phase is separated, washed with water and then extracted with 5% sodium hydroxide solution. The aqueous extract is separated and acidified and then extracted with ether. The ether extract is dried over sodium sulfate and the solvent removed using a rotary evaporator. The oily product is chromatographed using a column of silica gel (300 gm.) using a mixture of methanol and toluene (1:4, Vol.-/Vol.). Evaporation of pooled cuts of uniform composition gives 2.1 gm. of an oil which solidifies upon trituration with petroleum ether. Recrystallization from a mixture of ether (30 ml.) and petroleum ether (60 ml.) gives pure product m.p. 140°–142° C.

Analysis Calc. for $C_{18}H_{20}Cl_2O_4$: C, 58.23; H, 5.43%: Found: C, 58.33; H, 5.60%.

Step C:
3-[(6,7-Dichloro-2-cyclopentyl-2,3-dihydro-2-methyl-1-oxo-1H-inden-5-yl)oxy]propanamide The reaction is carried out as described in Example 1, Step C except that the (+)-(6,7-dichloro-2-cyclopentyl-2,3-dihydro-2-methyl-1-oxo-1H-inden-5-yl)acetic is replaced by an equimolar amount of 3-[(6,7-dichloro-2-cyclopentyl-2-methyl-1-oxo-1H-inden-5-yl)oxy]propanoic acid. There is thus obtained first 3-[(6,7-dichloro-2-cyclopentyl-2-methyl-1-oxo-1H-inden-5-yl)oxy]propanoyl chloride and, finally, 3-[(6,7-dichloro-2-cyclopentyl-2-methyl-1-oxo-1H-inden-5-yl)oxy]propanamide.

Step D:
3-[(6,7-Dichloro-2-cyclopentyl-2,3-dihydro-2-methyl-1-oxo-1H-inden-5-yl)oxymethyl]-4-hydroxy-1H-pyrrole-2,5-dione and its 1-Methylpiperazine Salt The reaction is conducted as described in Example 1, Step D except that the (+)-(6,7-dichloro-2-cyclopentyl-2,3-dihydro-2-methyl-1-oxo-1H-inden-5-yl)acetamide is replaced by an equimolar amount of 3-[(6,7-dichloro-2-cyclopentyl-2,3-dihydro-2-methyl-1-oxo-1H-inden-5-yl)oxy]propanamide. There is thus obtained 3-[(6,7-dichloro-2-cyclopentyl-2,3-dihydro-2-methyl-1-oxo-1H-inden-5-yl)oxymethyl]-4-hydroxy-1H-pyrrole-2,5-dione and its 1-methylpiperazine salt.

EXAMPLE 15

3-[2-((6,7-Dichloro-2-cyclopentyl-2,3-dihydro-2-methyl-1-oxo-1H-inden-5-yl)oxy)ethyl]-4-hydroxy-1H-pyrrole-2,5-dione and its 1-Methylpiperazine Salt Step A:
4-[(6,7-Dichloro-2-cyclopentyl-2,3-dihydro-2-methyl-1-oxo-1H-inden-5-yl)oxy]butyramide A stirred solution of 4-[(6,7-dichloro-2-cyclopentyl-2,3-dihydro-2-methyl-1-oxo-1H-inden-5-yl)oxy]butyric acid (7 g.,) and boron trifluoride-etherate (5 ml.) in methanol (50 ml.) is heated at reflux for 1 hour. The methanol is evaporated at reduced pressure, the residue dissolved in ether, washed with water, dried over $MgSO_4$ and evaporated at reduced pressure. The crude methyl ester thus obtained is dissolved in dimethylformamide (25 ml.), treated with methanol saturated with ammonia and stirred at 25° C. for 2 weeks. The 4-[(6,7-dichloro-2-cyclopentyl-2,3-dihydro-2-methyl-1-oxo-1H-iden-5-yl)oxy]butyramide is separated as white crystals melting at 138° C. and is used in Step B without further purification.

The 4-[(6,7-dichloro-2-cyclopentyl-2,3-dihydro-2-methyl-1-oxo-1H-inden-5-yl)oxy]butyramide is also prepared by treating a solution of 4-[(6,7-dichloro-2-cyclopentyl-2,3-dihydro-2-methyl-1-oxo-1H-inden-5-yl)oxy]butyric acid (3.85 g., 0.01 mole) in dry tetrahydrofuran (100 ml.) with 1,1'-carbonyldiimidazole (1.62 g., 0.01 mole) in tetrahydrofuran (25 ml) at 0° C., stirring for one hour and then treating with 25% aqueous ammonia (25 ml), stirring for 4 hours at 35° C., and removing the solvent to obtain the product.

Step B:
3-[2-((6,7-Dichloro-2-cyclopentyl-2,3-dihydro-2-methyl-1-oxo-1H-inden-5-yl)oxy)ethyl]-4-hydroxy-1H-pyrrole-2,5-dione and its 1-Methylpiperazine Salt To a stirred solution of 4-[(6,7-dichloro-2-cyclopentyl-2,3-dihydro-2-methyl-1-oxo-1H-inden-5-yl)oxy]butyramide (1.83 g., 4.8 mmole) and diethyl oxalate (0.7 ml., 5.2 mmole) cooled in an ice bath and in a nitrogen atmosphere is added potassium tert. butoxide (1.24 g., 11.1 mmole) in several portions during a 10 minute period. The reaction mixture is stirred at 25° C. overnight, poured into cold aqueous hydrochloric acid, extracted into ether, extracted into 2% potassium hydroxide, acidified with aqueous hydrochloric acid, extracted into ether, washed with water, dried over $MgSO_4$ and evaporated at reduced pressure. The residue is chromatographed on silica (40 g.,) and eluted with a mixture of methylene chloride, tetrahydrofuran and acetic acid (50:1:1). The pertinent fractions are evaporated at reduced pressure, the residue treated with toluene (50 ml) and evaporated to azeotrope the residual acetic acid. The residual oil is dissolved in ether (10 ml.) and methanol (0.5 ml.) then treated with 1-methylpiperazine to give 3-[2-((6,7-dichloro-2-cyclopentyl-2,3-dihydro-2-methyl-1-oxo-1H-inden-5-yl)oxy)ethyl]-4-hydroxy-1H-pyrrole-2,5-dione 1-methylpiperazine salt which melts at 191° C.

Analysis for $C_{21}H_{21}Cl_2NO_5 \cdot C_5H_{12}N_2$; Calc: C, 57.99; H, 6.18: N, 7.80; Found: C, 58.44; H, 6.56; N, 7.73%.

EXAMPLE 16

3-[3-((6,7-dichloro-2-cyclopentyl-2,3-dihydro-2-methyl-1-oxo-1H-inden-5-yl)oxy)propyl]-4-hydroxy-1H-pyrrole-2,5-dione and its 1-Methylpiperazine Salt Step A: Methyl
5-[(6,7-Dichloro-2-cyclopentyl-2,3-dihydro-2-methyl-1-oxo-1H-inden-5-yl)oxy]-pentanoate 2-Cyclopentyl-6,7-dichloro-2,3-dihydro-2-methyl-gydroxy-1H-inden-1-one (12 g., 0.04 mole) is dissolved in dimethylformamide (30 ml.) and treated with potassium carbonate (5.5 g., 0.04 mole). Methyl 5-bromopentanoate (8.5 g., 0.04 mole) is added dropwise with good stirring over a period of 30 minutes. Then, the mixture is stirred and heated in a steam bath for two hours. The mixture is cooled and poured in to ice water (300 ml.). The product which solidifies upon standing is removed by filtration. The yield is 15.1 g., m.p. 83°–86° C. Upon recrystallization from petroleum ether the methyl 5-[(6,7-dichloro-2-cyclopentyl-2,3-dihydro-2-methyl-1-oxo-1H-inden-5-yl)oxy]pentanoate melts at 85°–88° C.

Analysis: Calculated for $C_{21}H_{26}Cl_2O_4$: C, 61.02; H, 6.34: Found: C, 61.26; H, 6.64%.

Step B:
5[(6,7-Dichloro-2-cyclopentyl-2,3-dihydro-2-methyl-1-oxo-1H-inden-5-yl)oxy]pentanoic acid A mixture of methyl 5-[(6,7-dichloro-2-cyclopentyl-2,3-dihydro-2-methyl-1-oxo-1H-inden-5-yl)oxy]pentanoate (14 g., 0.0339 mole), acetic acid (100 ml) and 6N hydrochloric acid (50 ml) is stirred and refluxed for 6 hours. The mixture is poured into water (400 ml) and the product which solidifies upon standing is removed by filtration and dried. The product is recrystallized from a mixture of tetrahydrofuran, ether and petroleum ether (50/100/200 ml) to give 12.5 g, of 5-[6,7-dichloro- 2-cyclopentyl-2,3-dihydro-2-methyl-1-oxo-1H-inden-5-yl)oxy)pentanoic acid, m.p. 106°–108° C.

Analysis calculated for $C_{20}H_{24}Cl_2O_4$: C, 60.15; H, 6.06: Found: C, 60.19; H, 6.23%.

Steps C and D

These steps are carried out by following essentially the procedures described in Example 1, Steps C and D except that an equimolar amount of 5-[(6,7-dichloro-2-cyclopentyl-2,3-dihydro-2-methyl-1-oxo-1H-inden-5-yl)oxy]pentanoic acid is substituted for (+)-(6,7-dichloro-2-cyclopentyl-2,3-dihydro-2-methyl-1-oxo-1H-inden-5-yl)acetic acid that is used in Example 1, Step c. Thus, there is obtained in Step C 5-[(6,7-dichloro-2-cyclopentyl-2,3-dihydro-2-methyl-1-oxo-1H-inden-5-yl)oxy]pentanamide and in Step D, 3-[3-((6,7-dichloro-2-cyclopentyl-2,3-dihydro-2-methyl-1-oxo-1H-inden-5-yl)oxy)propyl]-4-hydroxy-1H-pyrrole-2,5-dione and its 1-methylpiperazine salt.

EXAMPLE 17

3-[4-((6,7-dichloro-2-cyclopentyl-2,3-dihydro-2-methyl-1-oxo-1H-inden-5-yl)oxy)butyl]-4-hydroxy-1H-pyrrole-2,5-dione and its 1-Methylpiperazine Salt Step A: Ethyl 6[(6,7-Dichloro-2-cyclopentyl-2,3-dihydro-2-methyl-1-oxo-1H-inden-5-yl)oxy]-hexanoate 6,7-Dichloro-2-cyclopentyl-2,3-dihydro-5-hydroxy-2-methyl-1H-inden-1-one (12 g., 0.04 mole) is dissolved in dimethylformamide (50 ml.), treated with potassium carbonate (5.5 g., 0.04 mole) and heated and stirred on a steam bath for 30 minutes. Ethyl 6-bromohexanoate (8.9 g., 0.04 mole) is added dropwise with good stirring over 15 minutes, then the mixture is heated and stirred in a steam bath for two hours. The reaction mixture is poured into water (400 ml.) and extracted with ether (2×150 ml.) The either extract is dried over sodium sulfate, filtered and the ether removed at reduced pressure. The residue, which crystalizes upon standing, is recrystallized from a mixture of ether and petroleum ether to give ethyl 6-[(6,7-dichloro-2-cyclopentyl-2,3-dihydro-2-methyl-1-oxo-1H-inden-5-yl)oxy]hexanoate, 16 g., m.p. 69°–72° C.

Analysis, calculated for $C_{23}H_{30}H_{30}Cl_2O_4$: C, 62.58; H, 6.85. Found: C, 62.78; H, 7.11%.

Step B: 6-[(6,7-Dichloro-2-cyclopentyl-2,3-dihydro-2-methyl-1-oxo-1H-inden-5-yl)oxy]hexanoic acid A mixture of ethyl 6-[(6,7-dichloro-2-cyclopentyl-2,3-dihydro-2-methyl-1-oxo-1H-inden-5-yl)oxy]hexanoate (16 g., 0.036 mole), acetic acid (100 ml.) and 6N hydrochloric acid (50 ml.) is stirred and refluxed for 6 hours. The mixture is poured into ice water (500 g.), extracted with ether, dried over $Na_2SO_4$, filtered and concentrated to a volume of 100 ml., and chilled. A total of 11.5 of 6-[6,7-dichloro-2-cyclopentyl-2,3-dihydro-2-methyl-1-oxo-1H-inden-5-yl)oxy]hexanoic acid separates, m.p. 127°–129° C.

Analysis, calculated for $C_{21}H_{26}Cl_2O_4$: C, 61.01; H, 6.34; Found: C, 61.03; H, 6.54%.

Steps C and D

These steps are carried out by following essentially the procedures described in Example 1, Steps C and D except that an equimolar amount of 6-[(6,7-dichloro-2-cyclopentyl-2,3-dihydro-2-methyl-1-oxo-1H-inden-5-yl)oxy]hexanoic acid is substituted for (+)-(6,7-dichloro-2-cyclopentyl-2,3-dihydro-2-methyl-1-oxo-1H-inden-5-yl)acetic acid that is used in Example 1, Step C. Thus, there is obtained in Step C 6-[(6,7-dichloro-2-cyclopentyl-2,3-dihydro-2-methyl-1-oxo-1H-inden-5-yl)oxy]hexanamide and in Step D, 3-[4-((6,7-dichloro-2-cyclopentyl-2,3-dihydro-2-methyl-1-oxo-1H-inden-5-yl)oxy)butyl]-4-hydroxy-1H-pyrrole-2,5-dione and its 1-methylpiperazine salt.

EXAMPLE 18

3-[5-((6,7-Dichloro-2-cyclopentyl-2,3-dihydro-2-methyl-1-oxo-1H-inden-5-yl)oxy)pentyl]-4-hydroxy-1H-pyrrole-2,5-dione and its 1-Methylpiperazine Salt Step A: Ethyl 7-[(6,7-Dichloro-2-cyclopentyl-2,3-dihydro-2-methyl-1-oxo-1H-inden-5-yl)oxy]heptanoate 6,7-Dichloro-2-cyclopentyl-2,3-dihydro-5-hydroxy-2-methyl-1H-inden-1-one (12 g., 0.04 mole) is dissolved in dimethylformamide (30 ml.), and potassium carbonate (5.5 g., 0.04 mole) is added and the mixture stirred and heated on a steam bath for 30 minutes. Ethyl 7-bromoheptanoate is added dropwise over 10 minutes with stirring and heating on a steam bath for two hours. The mixture is poured into a mixture of ice and water (300 g., total) and then extracted with ether. The ether extract is dried over $Na_2SO_4$, filtered and the ether removed at reduced pressure. The residue is dissolved in petroleum ether and cooled to −70° C. to obtain ethyl 7-[(6,7-dichloro-2-cyclopentyl-2,3-dihydro-2-methyl-1-oxo-1H-inden-5-yl)oxy]heptanoate, 17.7 g., m.p. 47°–50° C.

Analysis, calculated for $C_{24}H_{32}Cl_2O_4$: C, 63.29; H, 7.08; Found: C, 63.42; H, 7.35%.

Step B: 7-[(6,7-Dichloro-2-cyclopentyl-2,3-dihydro-2-methyl-1-oxo-1H-inden-5-yl)oxy]heptanoic acid A mixture of ethyl 7-[(6,7-Dichloro-2-cyclopentyl-2,3-dihydro-2-methyl-1-oxo-1H-inden-5-yl)oxy]heptanoate (16 g., 0.035 mole), acetic acid (100 ml.) and 6N hydrochloric acid (50 ml.) is stirred and refluxed for 6 hours. The mixture is poured into water (400 ml.) where upon the product slowly solidifies. The product is removed by filtration, dried and recrystallized from a mixture of tetrahydrofuran, ether and petroleum ether (50, 100 and 200 ml., respectively) to give 7-[(6,7-dichloro-2-cyclopentyl-2,3-dihydro-2-methyl-1-oxo-1H-inden-5-yl)oxy]heptanoic acid, 12.1 g., m.p. 107°–110° C.

Analysis, calculated for $C_{22}H_{28}Cl_2O_4$: C, 61.83; H, 6.60; Found: C, 61.93; H, 6.90%.

Steps C and D

These steps are carried out by following essentially the procedures described in Example 1, Steps C and D except that an equimolar amount of 7-[(6,7-dichloro-2-cyclopentyl-2,3-dihydro-2-methyl-1-oxo-1H-inden-5-yl)oxy]heptanoic acid, is substituted for the (+)-(6,7-dichloro-2-cyclopentyl-2,3-dihydro-2-methyl-1-oxo-1H-inden-5-yl)acetic acid used in Step C. Thus, there is obtained in Step C, 7-[(6,7-dichloro-2-cyclopentyl-2,3-dihydro-2-methyl-1-oxo-1H-inden-5-yl)oxy]heptanamide and in Step D, 3-[5-((6,7-dichloro-2-cyclopentyl-2,3-dihydro-2-methyl-1-oxo-1H-inden-5-yl)oxy)pentyl]-4-hydroxy-1H-pyrrole-2,5-dione and its 1-methylpiperazine salt.

EXAMPLE 19

3-(6,7-Dichloro-2-cyclopentyl-2,3-dihydro-1-hydroxy-2-methyl-1H-inden-5-yl)-4-hydroxy-1H-pyrrole-2,5-dione and its 1-Methylpiperazine Salt Step A:
(6,7-Dichloro-2-cyclopentyl-2,3-dihydro-1-hydroxy-2-methyl-1H-inden-5-yl)acetamide To a stirred solution of (6,7-dichloro-2-cyclopentyl-2,3-dihydro-2-methyl-1-oxo-1H-inden-5-yl)acetamide (6.8 g., 0.02 mole) in ethanol (100 ml) is added sodium borohydride (760 mg. 0.02 mole). After one hour another portion of sodium borohydride (760 mg, 0.021 mole) is added and stirring continued for 3 hours. The reaction mixture is poured into ice water and extracted with ethyl acetate. The ethyl acetate extract is washed with water and dried over magnesium sulfate. The ethyl acetate is evaporated at reduced pressure to give (6,7-dichloro-2-cyclopentyl-2,3-dihydro-1-hydroxy-2-methyl-1H-inden-5-yl)acetamide consisting of a mixture of two diastereomer, each of which is a racemate.

Step B:
3-(6,7-Dichloro-2-cyclopentyl-2,3-dihydro-1-hydroxy-2-methyl-1H-inden-5-yl)-4-hydroxy-1H-pyrrole-2,5-dione In an atmosphere of dry nitrogen, (6,7-dichloro-2-cyclopentyl-2,3-dihydro-1-hydroxy-2-methyl-1H-inden-5-yl)acetamide (7.8 g., 0.02 mole) diethyl oxalate (3.14 g., 0.0214 mole) and dimethylformamide (40 ml.) is stirred while cooling in an ice bath. Potassium tert.-butoxide (5.2 g., 0.046 mole) is added in two portions at 10 minute intervals. The mixture is then stirred at 25° C. for 18 hours, poured into water, acidified with hydrochloric acid, extracted into ether and the ether extract dried over magnesium sulfate. Evaporation of the ether at reduced pressure gives 3-(6,7-dichloro-2-cyclopentyl-2,3-dihydro-1-hydroxy-2-methyl-1H-inden-yl)-4-hydroxy-1H-pyrrole-2,5-dione as a mixture of two diastereomers. The mixture of two diastereomers is converted to its 1-methylpiperazine salt, m.p. 226-8.

Analysis, calculated for $C_{19}H_{19}Cl_2O_4 \cdot C_5H_{12}N_2$: C, 58.07; H, 6.29; N, 8.46; Found: C, 57.89; H, 6.40; N, 8.47; (which are separated by chromatography to two pure racemates designated as α-racemate and β-racemate).

EXAMPLE 20

3-[2-((6,7-Dichloro-2-cyclopentyl-2,3-dihydro-1-hydroxy-2-methyl-1H-inden-5-yl)oxy)ethyl]-4-hydroxy-1H-pyrrole-2,5-dione The preparation is carried out by following substantially the procedures described in Example 19, Steps A and B but substituting an equimolar amount of 4-[(6,7-dichloro-2-cyclopentyl-2,3-dihydro-2-methyl-1H-inden-5-yl)oxy]butyramide (Example 15, Step A) is substituted for the (6,7-dichloro-2-cyclopentyl-2,3-dihydro-2-methyl-1-oxo-1H-inden-5-yl)acetamide used in Example 19, Step A. Then, the product of Step A is used in Step B to obtain 3-[2-((6,7-dichloro-2-cyclopentyl-2,3-dihydro-1-hydroxy-2-methyl-1H-inden-5-yl)oxy)ethyl]-4-hydroxy-1H-pyrrole-2,5-dione as a mixture of two diastereomers each consisting of a racemate which are separated by chromatography to give the two pure racemates designated as α-racemate and β-racemate.

EXAMPLE 21

3-(7-Chloro-2-cyclopentyl-2,3-dihydro-2,6-dimethyl-1-oxo-1H-inden-5-yl)-4-hydroxy-1H-pyrrole-2,5-dione and its 1-Methylpiperazine Salt The preparation is carried out by following substantially the procedures described in Example 1, Steps A and D except that an equimolar amount of 7-chloro-2-cyclopentyl-2,3-dihydro-5-hydroxy-2,6-dimethyl-1H-inden-1-one is substituted for the (+)-(6,7-dichloro-2-cyclopentyl-2,3-dihydro-5-hydroxy-2-methyl-1H-inden-1-one used in Example 1, Step A. Then, the product of Steps A, B and C are used in each subsequent step (i.e., Steps B, C and D respectively) so that 3-(7-chloro-2-cyclopentyl-2,3-dihydro-2,6-dimethyl-1-oxo-1H-inden-5-yl)-4-hydroxy-1H-pyrrole-2,5-dione and its 1-methylpiperazine salt are obtained in Step D.

EXAMPLE 22

3-(2-Cyclopentyl-2,3-dihydro-2,6,7-trimethyl-1-oxo-1H-inden-5-yl)-4-hydroxy-1H-pyrrole-2,5-dione and its 1-Methylpiperazine Salt The preparation is carried out by following essentially the procedures described in Example 1, Steps A and D except that an equimolar amount of 2-cyclopentyl-2,3-dihydro-5-hydroxy-2,6,7-trimethyl-1H-inden-1-one is substituted for the (+)-(6,7-dichloro-2-cyclopentyl-2,3-dihydro-5-hydroxy-2-methyl-1H-inden-1-one used in Example 1, Step A. Then, the product of Steps A, B and C are used in each subsequent step (i.e., Steps B, C and D respectively) so that 3-(2-cyclopentyl-2,3-dihydro-2,6,7-trimethyl-1-oxo-1H-inden-5-yl)-4-hydroxy-1H-pyrrole-2,5-dione and its 1-methylpiperazine salt are obtained in Step D.

EXAMPLE 23

(−)-3-(6,7-Dichloro-2-cyclopentyl-2,3-dihydro-2-methyl-1-oxo-1H-inden-5-yl)-4-hydroxy-1H-pyrrole-2,5-dione and its 1-Methylpiperazine Salt The preparation is carried out by following substantially described in Example 1, Steps A and D substituting an equimolar amount of (−)6,7-dichloro-2-cyclopentyl-2,3-dihydro-5-hydroxy-2-methyl-1H-inden-1-one is substituted for the (+)-6,7-dichloro-2-cyclopentyl-2,3-dihydro-5-hydroxy-2-methyl-1H-inden-1-one used in Example 1, Step A. Then, the product of Steps A, B and C are used in each subsequent step so that (−)-3-(6,7-dichloro-2-cyclopentyl-2,3-dihydro-2-methyl-1-oxo-1H-inden-5-yl)-4-hydroxy-1H-pyrrole-2,5-dione and its 1-methylpiperazine salt are obtained in Step D. The melting point of the 1-methylpiperazine salt is 203°–204° C.

Analysis, calculated for $C_{24}H_{29}Cl_2N_3O_4$: C, 58.30; H, 5.91; N, 8.50%. Found: C, 58.37; H, 6.02; N, 8.61%;

EXAMPLE 24

(+)-[6,7-Dichloro-2,3-dihydro-2-methyl-2-(1-methylethyl)-1-oxo-1H-inden-5-yl]-4-hydroxy-1H-pyrrole-2,5-dione and its 1-Methylpiperazine Salt Step A:
(+)6,7-Dichloro-2,3-dihydro-2-methyl-2-(1-methylethyl)-1-oxo-1H-inden-1-one The preparation is conducted essentially as described in Example 5, Step B except that an equimolar amount of (+)(6,7-dichloro-2,3-dihydro-2-methyl-2-(1-methylethyl)-1-oxo-1H-inden-5-yl)acetic acid is substituted for the 6,7-dichloro-2-cyclopentylmethyl-2,3-dihydro-5-methoxy-2-methyl-1H-inden-1-one that is used in Example 5, Step B. There is thus obtained in (+)-6,7-dichloro-2,3-dihydro-5-hydroxy-2-methyl-2-(1-methylethyl)-1H-inden-1-one.

Steps B, C, D and E

The synthesis is carried out essentially as described in Example 1, Steps A through D except that an equimolar amount of (+)-6,7-dichloro-2,3-dihydro-5-hydroxy-2-methyl-2-(1-methylethyl)-1H-inden-1-one is substituted for the (+)-6,7-dichloro-2-cyclopentyl-2,3-dihydro-5-hydroxy-2-methyl-1H-inden-1-one that is used in Example 1, Step A. Then, the products of Step B, C and D are used in each subsequent step (i.e., Steps C, D and E) so that (+)-6,7-dichloro-2,3-dihydro-2-methyl-2-(1-methylethyl)-1-oxo-1H-inden-5-yl)-4-hydroxy-1H-pyrrole-2,5-dione-1-methylpiperazine salt is obtained in Step E.

EXAMPLE 25

(−)[6,7-Dichloro 2,3-dihydro-2-methyl-2-(1-methylethyl)-1-oxo-1H-inden-5-yl-4-hydroxy-1H-pyrrole-2,5-dione and its 1-Methylpiperazine Salt Step A: (−)[6,7-Dichloro 2,3-dihydro-2-methyl-5-hydroxy-2-(1-methylethyl)-1H-inden-1-one The preparation is carried out essentially as described in Example 5, Step B except that an equimolar amount of (−)(6,7-dichloro-2,3-dihydro-2-methyl-2-(1-methylethyl)-1-oxo-1H-inden-5-yl)oxy]acetic acid is substituted for the 6,7-dichloro-2-cyclo-pentylmethyl-2,3-dihydro-5-methoxy-2-methyl-1H-inden-1-one that is used in Example 5, Step B. There is thus obtained (−)-6,7-dichloro-2,3-dihydro-5-hydroxy-2-methyl-2-(1-methylethyl)-1H-inden-1-one.

Steps B, C, D

These synthetic steps are carried out essentially as described in Example 1, Steps A through D except that an equimolar amount of (−)-6,7-dichloro-2,3-dihydro-5-hydroxy-2-methyl-2-(1-methylethyl)-1H-inden-1-one is substituted for the (+)-6,7-dichloro-2-cyclopentyl-2,3-dihydro-5-hydroxy-2-methyl-1H-inden-1-one used in Example 1, Step A. Then, the products of Step B, C and D are used in each subsequent step (i.e., Steps C and D) so that (−)-[6,7-dichloro-2,3-dihydro-2-methyl-2-(1-methylethyl)-1-oxo-1H-inden-5-yl]-4-hydroxy-1H-pyrrole-2,5-dione and its 1-methylpiperazine salt are obtained in Step D.

EXAMPLE 26

(+)-(2-Butyl-6,7-dichloro-2-cyclopentyl-2,3-dihydro-1-oxo-1H-inden-5-yl)-4-hydroxy-1H-pyrrole-2,5-dione and its 1-Methylpiperazine Salt The preparation is conducted essentially as described in Example 1, Steps A though D except that (+)-2-butyl-6,7-dichloro-2-cyclopentyl-2,3-dihydro-5-hydroxy-1H-inden-1-one is substituted for the (+)-6,7-dichloro-2-cyclopentyl-2,3-dihydro-5-hydroxy-2-methyl-1H-inden-1-one used in Example 1, Step A. Then, the products of Step A, B and C are used in each subsequent step (i.e., Steps B, C and D) so that (+)-(2-butyl-6,7-dichloro-2-cyclopentyl-2,3-dihydro-1-oxo-1H-inden-5-yl)-4-hydroxy-1H-pyrrole-2,5-dione and its 1-methylpiperazine salt are obtained in Step D.

EXAMPLE 27

(−)-(2-Butyl-6,7-dichloro-2-cyclopentyl-2,3-dihydro-1-oxo-1H-inden-5-yl)-4-hydroxy-1H-pyrrole-2,5-dione and its 1-Methylpiperazine Salt The preparation is conducted essentially as described in Example 1. Steps A though D except that (−)-2-butyl-6,7-dichloro-2-cyclopentyl-2,3-dihydro-5-hydroxy-1H-inden-1-one is substituted for the (+)-6,7-dichloro-2-cyclopentyl-2,3-dihydro-5-hydroxy-2-methyl-1H-inden-1-one used in Example 1, Step A. Then, the products of Step A, B and C are used in each subsequent step (i.e., Steps B, C and D) so that (−)-(2-butyl-6,7-dichloro-2-cyclopentyl-2,3-dihydro-1-oxo-1H-inden-5-yl)-4-hydroxy-1H-pyrrole-2,5-dione and its 1-methylpiperazine salt are obtained in Step D.

EXAMPLE 28

(+)-(6,7-Dichloro-2,3-dihydro-2-methyl-1-oxo-2-phenyl-1H-inden-5-yl)-4-hydroxy-1H-pyrrole-2,5-dione and its 1-Methylpiperazine Salt The preparation is carried out substantially as described in Example 1, Steps A though D except that (+)-6,7-dichloro-2,3-dihydro-5-hydroxy-2-methyl-2-phenyl-1H-inden-1-one is substituted for the (+)-6,7-dichloro-2-cyclopentyl-2,3-dihydro-5-hydroxy-2-methyl-1H-inden-1-one that is used in Example 1, Step A. Then, the products of Step A, B and C are used in each subsequent step (i.e., Steps B, C and D) so that (+)-(6,7-dichloro-2,3-dihydro-2-methyl-1-oxo-2-phenyl-1H-inden-5-yl)-4-hydroxy-1H-pyrrole-2,5-dione and its 1-methylpiperazine salt are obtained in Step D.

EXAMPLE 29

(−)-(6,7-Dichloro-2,3-dihydro-2-methyl-1-oxo-2-phenyl-1H-inden-5-yl)-4-hydroxy-1H-pyrrole-2,5-dione and its 1-Methylpiperazine Salt The preparation is carried out substantially as described in Example 1, Steps A through D except that (−)-6,7-dichloro-2,3-dihydro-5-hydroxy-2-methyl-2-phenyl-1H-inden-1-one is substituted for the (+)-6,7-dichloro-2-cyclopentyl-2,3-dihydro-5-hydroxy-2-methyl-1H-inden-1-one that is used in Example 1, Step A. Then, the products of Step A, B and C are used in each subsequent step (i.e., Steps B, C and D) so that (−)-(6,7-dichloro-2,3-dihydro-2-methyl-1-oxo-2-phenyl-1H-inden-5-yl)-4-hydroxy-1H-pyrrole-2,5-dione and its 1-methylpiperazine salt are obtained in Step D.

EXAMPLE 30

(+)-3-[2-(((6,7-Dichloro-2-cyclopentyl-2,3-dihydro-2-methyl-1-oxo-1H-inden-5-yl)oxy)ethyl]-4-hydroxy-1H-pyrrole-2,5-dione and its 1-Methylpiperazine Salt The preparation is carried out substantially as described in Example 15, Steps A and B except that (+)-[(6,7-dichloro-2-cyclopentyl-2,3-dihydro-2-methyl-1-oxo-1H-inden-5-yl)oxy]butyric acid is substituted for the corresponding racemic compound used in Example 15, Step A. There is obtained in Step A, (+)-4-[((6,7-dichloro-2-cyclopentyl-2,3-dihydro-2-methyl-1-oxo-1H-inden-5-yl)oxy]butyramide which is then used in Step B in place of the corresponding racemic compound to obtain (+)3-[2-((6,7-dichloro-2 -cyclopentyl-2,3-dihydro-2-methyl-1-oxo-1H-inden-5-yl)oxy)ethyl]-

4-hydroxy-1H-pyrrole-2,5-dione and its 1-methylpiperazine salt.

EXAMPLE 31

(−)3-[2((6,7-Dichloro-2-cyclopentyl-2,3-dihydro-2-methyl-1-oxo-1H-inden-5-yl)oxy)ethyl]-4-hydroxy-1H-pyrrole-2,5-dione and its 1-Methylpiperazine Salt The preparation is carried out substantially as described in Example 15, Steps A and B except that (−)-4-[(6,7-dichloro-2-cyclopentyl-2,3-dihydro-2-methyl-1-oxo-1H-inden-5-yl)oxy]butyric acid is substituted for the corresponding racemic compound used in Example 15, Step A. There is obtained in Step A, (−)-4[(6,7-dichloro-2-cyclopentyl-2,3-dihydro-2-methyl-1-oxo-1H-inden-5-yl)oxy]butyramide which is then used in Step B in place of the corresponding racemic compound to obtain (−)3-[2-((6,7-dichloro-2-cyclopentyl-2,3-dihydro-2-methyl-1-oxo-1H-inden-5-yl)oxy)ethyl]-4-hydroxy-1H-pyrrole-2,5-dione and its 1-methylpiperazine salt.

EXAMPLE 32

(+)-Enantiomers of the two diastereomers of 3-(6,7-dichloro-2-cyclopentyl-2,3-dihydro-1-hydroxy-2-methyl-1H-inden-5-yl)-4-hydroxy-1H-pyrrole-2,5-dione Step A: (+)-Enantiomers of the two diastereomers of (6,7-dichloro-2-cyclopentyl-2,3-dihydro-1-hydroxy-2-methyl-1H-inden-5-yl)acetamide To a stirred solution of (+)-(6,7-dichloro-2-cyclopentyl-2,3-dihydro-2-methyl-1-oxo-1H-inden-5-yl)acetamide (3.4 g, 0.01 mole) in ethanol (50 ml) is added sodium borohydride (380 mg, 0.01 mole). After one hour, another portion of sodium borohydride (380 mg, 0.01 mole) is added. The reaction is stirred for 3 hours, poured into ice water, extracted with ethyl acetate, washed with water and dried over magnesium sulfate. Evaporation of the ethyl acetate gives a mixture of the (+)-enantiomers of the two diastereomers of (6,7-dichloro-2-cyclopentyl-2,3-dihydro-1-hydroxy-2-methyl-1H-inden-5-yl)acetamide.

Step B: (+)-Enantiomers of the two diastereomers of 3-(6,7-dichloro-2-cyclopentyl-2,3-dihydro-1-hydroxy-2-methyl-1H-inden-5-yl)-4-hydroxy-1H-pyrrole-2,5-dione In an atmosphere of dry nitrogen, a mixture of the (+)-enantiomers of the two diastereomers of (6,7-dichloro-2-cyclopentyl-2,3-dihydro-1-hydroxy-2-methyl-1H-inden-5-yl)acetamide (3.4 g, 0.01 mole) and diethyl oxalate (1.57 g, 0.0107 mole) are dissolved in dimethylformamide (20 ml) and stirred in an ice bath. Potassium tert. butoxide (2.6 g, 0.023 mole) is added in 2 portions at a 10 minute interval. The reaction mixture is stirred at 25° for 18 hours, poured into water, acidified with hydrochloric acid, extracted into ether, washed with water and dried over magnesium sulfate. Evaporation of the ether at reduced pressure gives a mixture of the two (+)-enantiomers of the two diastereomers of 3-(6,7-dichloro-2-cyclopentyl-2,3-dihydro-1-hydroxy-2-methyl-1H-inden-5-yl)-4-hydroxy-1H-pyrrole-2,5-dione. Each of these two diastereomers consists of one enantiomer which are separated by chromatography to give the two pure diastereomers designated as the (+)-α-diastereomer and (+)-β-diastereomer.

EXAMPLE 33

(+)-Enantiomers of the two diastereomers of (+)-3-[2-((6,7-dichloro-2-cyclopentyl-2,3-dihydro-1-hydroxy-2-methyl-1H-inden-5-yl)oxy)ethyl]-4-hydroxy-1H-pyrrole-2,5-dione Step A: (+)-Enantiomers of the two diastereomers of 4-[(6,7-dichloro-2-cyclopentyl-2,3-dihydro-2-methyl-1-oxo-1H-inden-5-yl)oxy]butyramide The preparation is carried out essentially as described in Example 15, Step A except that (+)-4-[(6,7-dichloro-2-cyclopentyl-2,3-dihydro-2-methyl-1-oxo-1H-inden-5-yl)oxy]butyric acid is substituted for the corresponding racemate used in Example 15, Step A. There is thus obtained (+)-enantiomers of the two diastereomer of 4-[(6,7-dichloro-cyclopentyl-2,3-dihydro-2-methyl-1-oxo-1H-inden-5-yl)oxy]butyramide.

Step B: (+)-Enantiomers of the two diastereomers of 4-[(6,7-Dichloro-2-cyclopentyl-2,3-dihydro-1-hydroxy-1-methyl-1H-inden-5-yl)oxy]butyramide The synthesis is conducted substantially as described in Example 19, Step A except that an equimolar amount of a mixture of the two (+)-enantiomers of the two diastereomers of 4-[(6,7-dichloro-2-cyclopentyl-2,3-dihydro-2-methyl-1-oxo-1H-inden-5-yl)oxy]butyramide is substituted for the (6,7-dichloro-2-cyclopentyl-2,3-dihydro-2-methyl-1-oxo-1H-inden-5-yl)-acetamide that is used in Example 19, Step A. There is thus obtained (+)-enantiomers of the two diastereomers of 4-[(6,7-dichloro-2-cyclopentyl-2,3-dihydro-1-hydroxy-1-methyl-1H-inden-5-yl)oxy]butyramide.

Step C: (+)-Enantiomers of the two diastereomers of 3-[2-((6,7-dichloro-2-cyclopentyl-2,3-dihydro-1-hydroxy-2-methyl-1H-inden-5-yl)oxy)ethyl]4-hydroxy-1H-pyrrole-2,5-dione The preparation is conducted substantially as described in Example 1, Step D except that an equimolar amount of the two (+)-enantiomers of the two diastereomers of 4-[(6,7-dichloro-2-cyclopentyl-2,3-dihydro-1-hydroxy-2-methyl-1H-inden-5-yl)oxy]butylamide is substituted for the (+)-(6,7-dichloro-2-cyclopentyl-2,3-dihydro-2-methyl-1-oxo-1H-inden-5-yl)acetamide used in Example 1, Step D. There is thus obtained a mixture of the (+)-enantiomers of the two diastereomers of 3-[2-((6,7-dichloro-2-cyclopentyl-2,3-dihydro-1-hydroxy-2-methyl-1H-inden-5-yl)oxy)-ethyl]-4-hydroxy-1H-pyrrole-2,5-dione. Each diastereomer consists of one pure enantiomer which are separated by chromatography to give the two pure diastereomers designated as (+)-α-diastereomer and (+)-β-diastereomer since they were derived from the (+)-enantiomer described in Step A.

EXAMPLE 34

(+)-Enantiomers of the diastereomers of 3-[(6,7-dichloro-2-cyclopentyl-2,3-dihydro-1-hydroxy-2-methyl-1H-inden-5-yl)oxy]-4-hydroxy-1H-pyrrole-2,5-dione Step A: (+)-Enantiomers of the diastereomers of [(6,7-dichloro-2-cyclopentyl-2,3-dihydro-2-methyl-1-oxo-1H-inden-5-yl)oxy]acetamide The preparation is carried out by following substantially the procedures described in Example 1, Step C except that an equimolar amount of (+)-[(6,7-dichloro- 2-cyclopentyl-2,3-dihydro-2-methyl-1-oxo-1H-inden-5-yl)oxy]acetic acid is substituted for the (+)-(6,7-dichloro-2-cyclopentyl-2,3-dihydro-2-methyl-1-oxo-1H-inden-5-yl)acetic acid used in Example 1, Step C. There is thus obtained first the (+)-enantiomers of the diastereomers of [(6,7-dichloro-2-cyclopentyl-2,3-dihydro-2-methyl-1-oxo-1H-inden-5-yl)oxy]acetyl chloride and then (+)-enantiomers of the diastereomers of [(6,7-dichloro-2-cyclopentyl-2,3-dihydro-2-methyl-1-oxo-1H-inden-5-yl)oxy]acetamide.

Step B: (+)-Enantiomers of the diastereomers of [(6,7-dichloro-2-cyclopentyl-2,3-dihydro-1-hydroxy-2-methyl-1H-inden-5-yl)oxy]acetamide The preparation is carried out by following substantially the procedures described in Example 19, Step A, except that an equimolar amount of (+)-enantiomers of the diastereomers of [(6,7-dichloro-2-cyclopentyl-2,3-dihydro-2-methyl-1-oxo-1H-inden-5-yl)oxy]acetamide is substituted for the (6,7-dichloro-2-cyclopentyl-2,3-dihydro-2-methyl-1-oxo-1H-inden-5-yl)acetamide used in Example 19, Step A. There is thus obtained (+)-enantiomers of the (+)-diastereomers of [(6,7-dichloro-2-cyclopentyl-2,3-dihydro-1-hydroxy-2-methyl-1H-inden-5-yl)oxy]acetamide.

Step C: (+)-Enantiomers of the diastereomers of 3-[(6,7-dichloro-2-cyclopentyl-2,3-dihydro-1-hydroxy-2-methyl-1H-inden-5-yl)oxy]-4-hydroxy-1H-pyrrole-2,5-dione The preparation is carried out by following substantially the procedures described in Example 1, Step D, except that an equimolar amount of (+)-enantiomers of the diastereomers of [(6,7-dichloro-2-cyclopentyl-2,3-dihydro-1-hydroxy-2-methyl-1H-inden-5-yl)oxy]acetamide is substituted for the (+)-(6,7-dichloro-2-cyclopentyl-2,3-dihydro-2-methyl-1-oxo-1H-inden-5-yl)acetamide used in Example 1, Step D. There is thus obtained a mixture of the (+)-enantiomers of the diastereomers of 3-[(6,7-dichloro-2-cyclopentyl-2,3-dihydro-1-hydroxy-2-methyl-1H-inden-5-yl)oxy]-4-hydroxy-1H-pyrrole-2,5-dione which consists of two diastereomers each of which are composed of a pure enantiomer. These diastereomers are separated by chromatography to give the pure diastereomers which are designated as (+)-α-diastereomer and the (+)-β-diastereomer since they are derived from the (+)-enantiomer described in Step A.

EXAMPLE 35

Parenteral Solution of the 1-Methylpiperazine Salt of (+)-3-(6,7-dichloro-2-cyclopentyl-2,3-dihydro-2-methyl-1-oxo-1H-inden-5-yl)-4-hydroxy-1H-pyrrole-2,5-dione (+)-3-(6,7-Dichloro-2-cyclopentyl-2,3-dihydro-2-methyl-1-oxo-1H-inden-5-yl)-4-hydroxy-1H-pyrrole-2,5-dione 1-methylpiperazine salt (Example 1, Step D) (125.4 mg) is dissolved by stirring and warming with a sufficient volume of pyrogen-free water to give a final volume of 20 ml. The solution is then sterilized by filtration, the concentration of the active agent in the final solution is 0.5%.

EXAMPLE 36

Parenteral Solution of the Sodium Salt of (+)-3-(6,7-dichloro-2-cyclopentyl-2,3-dihydro-2-methyl-1-oxo-1H-inden-5-yl)-4-hydroxy-1H-pyrrole-2,5-dione (+)-3-(6,7-Dichloro-2-cyclopentyl-2,3-dihydro-2-methyl-1-oxo-1H-inden-5-yl)-4-hydroxy-1H-pyrrole-2,5-dione (Example 1, Step D) (500 mg) is dissolved by stirring and warming with 0.25N sodium bicarbonate (5.4 ml). The solution is diluted to 10 ml and sterilized by filtration. All the water that is used in the preparation is pyrogen-free. The concentration of the active agent in the final solution is 5%.

EXAMPLE 37

Parenteral Solution of the Sodium Salt of (+)-(2-butyl-6,7-dichloro-2-cyclopentyl-2,3-dihydro-1-oxo-1H-inden-5-yl)-4-hydroxy-1H-pyrrole-2,5-dione (+)-(2-Butyl-6,7-dichloro-2-cyclopentyl-2,3-dihydro-1-oxo-1H-inden-5-yl)-4-hydroxy-1H-pyrrole-2,5-dione (Example 26, Step D) (500 mg) is dissolved by stirring and warming with 0.25N sodium bicarbonate (5 ml). The solution is diluted to 10 ml and sterilized by filtration. All the water that is used in the preparation is pyrogen-free. The concentration of the active agent in the final solution is 5%.

EXAMPLE 38

Parenteral Solution of Sodium Salt of (+)-3-[2-((6,7-dichloro-2-cyclopentyl-2,3-dihydro-2-methyl-1-oxo-1H-inden-5-yl)oxy)ethyl]-4-hydroxy-1H-pyrrole-2,5-dione (+)-3-[2-((6,7-Dichloro-2-cyclopentyl-2,3-dihydro-2-methyl-1-oxo-1H-inden-5-yl)oxy)ethyl]-4-hydroxy-1H-pyrrole-2,5-dione (Example 30, Step B) (500 mg) is dissolved by stirring and warming with 0.05N sodium bicarbonate solution (4.9 ml). The solution is diluted to 10 ml and sterilized by filtration. All the water that is used in the preparation is pyrogen-free. The concentration of the active agent in the final solution is 5%.

EXAMPLE 39

Parenteral Solution of the Sodium Salt of (−)-(6,7-dichloro-2,3-dihydro-2-methyl-1-oxo-2-phenyl-1H-inden-5-yl)-4-hydroxy-1H-pyrrole-2,5-dione (−)-(6,7-Dichloro-2,3-dihydro-2-methyl-1-oxo-2-phenyl-1H-inden-5-yl)-4-hydroxy-1H-pyrrole-2,5-dione (Example 29, Step D) (500 mg) is dissolved by stirring and warming with 0.25N sodium bicarbonate solution (5.4 ml). The solution is diluted to 10 ml and sterilized by filtration. All the water that is used in the preparation is pyrogen-free. The concentration of the active agent in the final solution is 5%.

Similar parenteral solutions can be prepared by replacing the active ingredient of the above example by any of the other 4-hydroxy-1H-pyrrole-2,5-dione compounds of this invention.

EXAMPLE 40

Dry-Filled Capsules Containing 100 mg of Active Ingredient Per Capsule

|  | Per Capsule |
|---|---|
| (+)-3-(6,7-Dichloro-2-cyclo- | 100 mg |

-continued

| | Per Capsule |
|---|---|
| pentyl-2,3-dihydro-2-methyl-1-oxo-1H—inden-5-yl)-4-hydroxy-1H—pyrrole-2,5-dione | |
| Lactose | 99 mg |
| Magnesium Stearate | 1 mg |
| Capsule (Size No. 1) | 200 mg |

The (+)-3-(6,7-dichloro-2-cyclopentyl-2,3-dihydro-2-methyl-1-oxo-1H-inden-5-yl)-4-hydroxy-1H-pyrrole-2,5-dione (Example 1, Step D) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 41

Dry-Filled Capsules Containing 100 mg of Active Ingredient Per Capsule

| | Per Capsule |
|---|---|
| (+)-(2-Butyl-6,7-dichloro-2-cyclopentyl-2,3-dihydro-1-oxo-1H—inden-5-yl)-4-hydroxy-1H—pyrrole-2,5-dione | 100 mg |
| Lactose | 99 mg |
| Magnesium Stearate | 1 mg |
| Capsule (Size No. 1) | 200 mg |

The (+)-(2-butyl-6,7-dichloro-2-cyclopentyl-2,3-dihydro-1-oxo-1H-inden-5-yl)-4-hydroxy-1H-pyrrole-2,5-dione (Example 26, Step D) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 42

Dry-Filled Capsules Containing 100 mg of Active Ingredient Per Capsule

| | Per Capsule |
|---|---|
| (+)-3-[2-((6,7-dichloro-2-cyclopentyl-2,3-dihydro-2-methyl-1-oxo-1H—inden-5-yl)oxy)ethyl]-4-hydroxy-1H—pyrrole-2,5-dione | 100 mg |
| Lactose | 99 mg |
| Magnesium Stearate | 1 mg |
| Capsule (Size No. 1) | 200 mg |

The (+)-3-[2-((6,7-dichloro-2-cyclopentyl-2,3-dihydro-2-methyl-1-oxo-1H-inden-5-yl)oxy)ethyl]-4-hydroxy-1H-pyrrole-2,5-dione (Example 30, Step B) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 43

Dry-Filled Capsules Containing 100 mg of Active Ingredient Per Capsule

| | Per Capsule |
|---|---|
| (−)-(6,7-Dichloro-2,3-dihydro-2-methyl-1-oxo-2-phenyl-1H—inden-5-yl)-4-hydroxy-1H—pyrrole-2,5-dione | 100 mg |
| Lactose | 99 mg |
| Magnesium Stearate | 1 mg |
| Capsule (Size No. 1) | 200 mg |

The (−)-(6,7-dichloro-2,3-dihydro-2-methyl-1-oxo-2-phenyl-1H-inden-5-yl)-4-hydroxy-1H-pyrrole-2,5-dione (Example 29, Step D) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar dry-filled capsules can be prepared by using any of the other compounds of this invention.

What is claimed is:

1. A method of treating persons with gray matter edema which comprises administering to such a person an effective amount of a compound of the formula:

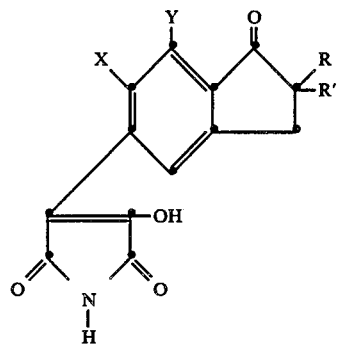

in which R and R' are different entities and wherein

R is $C_3$–$C_6$ cycloalkyl, $C_4$–$C_7$ cycloalkyl-lower alkyl, aryl selected from phenyl, halophenyl, methoxyphenyl, hydroxyphenyl, heterocyclic including thienyl, aralkyl selected from benzyl and phenethyl, $C_1$–$C_4$ lower alkyl, lower alkenyl or lower alkynyl;

R' is $C_1$–$C_4$ lower alkyl, lower alkenyl or lower alkynyl;

X and Y are each selected from methyl and chloro.

* * * * *